(12) United States Patent
Gross et al.

(10) Patent No.: US 9,757,574 B2
(45) Date of Patent: Sep. 12, 2017

(54) DUAL CHAMBER TRANSVENOUS PACEMAKER

(71) Applicant: RAINBOW MEDICAL, LTD., Herzliya (IL)

(72) Inventors: Yossi Gross, Moshav Mazor (IL); Zev Sohn, Ginot Shomron (IL); Roy Katz, Lincoln, MA (US)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 14/709,380

(22) Filed: May 11, 2015

(65) Prior Publication Data

US 2016/0331958 A1  Nov. 17, 2016

(51) Int. Cl.
 *A61N 1/368* (2006.01)
 *A61N 1/375* (2006.01)
 *A61N 1/05* (2006.01)

(52) U.S. Cl.
 CPC ............. *A61N 1/375* (2013.01); *A61N 1/057* (2013.01); *A61N 1/368* (2013.01)

(58) Field of Classification Search
 CPC .... A61N 1/056; A61N 1/0563; A61N 1/0585; A61N 1/0587; A61N 1/362; A61N 1/3622; A61N 1/368; A61N 1/3684
 USPC .............................. 607/9, 115, 116, 119, 122
 See application file for complete search history.

(56) References Cited

U.S. PATENT DOCUMENTS

| | | |
|---|---|---|
| 3,874,388 A | 4/1975 | King et al. |
| 4,391,124 A | 7/1983 | Drost et al. |
| 4,407,296 A | 10/1983 | Anderson |
| 4,485,813 A | 12/1984 | Anderson et al. |
| 4,492,107 A | 1/1985 | Sandhu |

(Continued)

FOREIGN PATENT DOCUMENTS

| | | |
|---|---|---|
| EP | 0897690 | 2/1999 |
| EP | 0928598 | 8/2000 |

(Continued)

OTHER PUBLICATIONS

Goodall, E (1996) Position-Selective Activation of Peripheral Nerve Fibers with a Cuff Electrode.

(Continued)

*Primary Examiner* — Allen Porter, Jr.
(74) *Attorney, Agent, or Firm* — Sughrue Mion, PLLC

(57) ABSTRACT

Apparatus and methods are described, including apparatus for pacing a heart of a subject. The apparatus includes an implantable pulse generator (IPG) and a coiled lead connected to the IPG. The coiled lead includes a smaller-diameter coiled portion, a lumen of which having a first coil-lumen-diameter, and a larger-diameter coiled portion electrically in series with the smaller-diameter coiled portion, a lumen of the larger-diameter coiled portion having a second coil-lumen-diameter that is larger than the first coil-lumen-diameter. A perpendicular distance from a central longitudinal axis of the smaller-diameter coiled portion to the lumen of the larger-diameter coiled portion is greater than an outer radius of the smaller-diameter coiled portion, when the central longitudinal axis of the smaller-diameter coiled portion is parallel to a central longitudinal axis of the larger-diameter coiled portion. Other applications are also described.

21 Claims, 18 Drawing Sheets

(56) References Cited

U.S. PATENT DOCUMENTS

| | | |
|---|---|---|
| 4,672,976 A | 6/1987 | Kroll |
| 4,836,204 A | 6/1989 | Landymore et al. |
| 4,846,191 A | 7/1989 | Brockway et al. |
| 4,900,303 A | 2/1990 | Lemelson |
| 4,917,089 A | 4/1990 | Sideris |
| 4,966,148 A | 10/1990 | Millar |
| 5,040,538 A | 8/1991 | Mortazavi |
| 5,218,965 A | 6/1993 | Ring |
| 5,284,138 A | 2/1994 | Kujawski |
| 5,303,207 A | 4/1994 | Brady et al. |
| 5,334,217 A | 8/1994 | Das |
| 5,411,551 A | 5/1995 | Winston et al. |
| 5,415,630 A | 5/1995 | Gory et al. |
| 5,451,235 A | 9/1995 | Lock et al. |
| 5,634,936 A | 6/1997 | Linden et al. |
| 5,656,036 A | 8/1997 | Palmaz |
| 5,662,711 A | 9/1997 | Douglas |
| 5,704,352 A | 1/1998 | Tremblay et al. |
| 5,725,552 A | 3/1998 | Kotula et al. |
| 5,733,313 A | 3/1998 | Barreras, Sr. et al. |
| 5,772,669 A | 6/1998 | Vrba |
| 5,775,331 A | 7/1998 | Raymond et al. |
| 5,824,053 A | 10/1998 | Khosravi et al. |
| 5,833,603 A | 11/1998 | Kovacs et al. |
| 5,855,563 A | 1/1999 | Kaplan et al. |
| 5,860,923 A | 1/1999 | Lenker et al. |
| 5,891,154 A | 4/1999 | Loeffler |
| 5,967,980 A | 10/1999 | Ferre et al. |
| 5,967,986 A | 10/1999 | Cimochowski et al. |
| 5,967,989 A | 10/1999 | Cimochowski et al. |
| 6,002,969 A | 12/1999 | Machek et al. |
| 6,015,386 A | 1/2000 | Kensey et al. |
| 6,015,387 A | 1/2000 | Schwartz et al. |
| 6,030,413 A | 2/2000 | Lazarus |
| 6,033,366 A | 3/2000 | Brockway et al. |
| 6,053,873 A | 4/2000 | Govari et al. |
| 6,076,016 A | 6/2000 | Feierbach |
| 6,097,984 A | 8/2000 | Douglas |
| 6,106,464 A | 8/2000 | Bass et al. |
| 6,140,740 A | 10/2000 | Porat et al. |
| 6,159,156 A | 12/2000 | Van Bockel |
| 6,179,858 B1 | 1/2001 | Squire et al. |
| 6,193,745 B1 | 2/2001 | Fogarty et al. |
| 6,214,025 B1 | 4/2001 | Thistle et al. |
| 6,236,889 B1 | 5/2001 | Soykan et al. |
| 6,239,724 B1 | 5/2001 | Doron et al. |
| 6,246,898 B1 | 6/2001 | Vesely et al. |
| 6,277,078 B1 | 8/2001 | Porat et al. |
| 6,278,790 B1 | 8/2001 | Davis et al. |
| 6,309,350 B1 | 10/2001 | VanTassel et al. |
| 6,328,699 B1 | 12/2001 | Eigler et al. |
| 6,331,163 B1 | 12/2001 | Kaplan |
| 6,379,308 B1 | 4/2002 | Brockway et al. |
| 6,409,674 B1 | 6/2002 | Brockway et al. |
| 6,416,474 B1 | 7/2002 | Penner et al. |
| 6,432,050 B1 | 8/2002 | Porat et al. |
| 6,442,413 B1 | 8/2002 | Silver |
| 6,447,522 B2 | 9/2002 | Gambale et al. |
| 6,475,170 B1 | 11/2002 | Doron et al. |
| 6,486,588 B2 | 11/2002 | Doron et al. |
| 6,527,780 B1 | 3/2003 | Wallace et al. |
| 6,543,272 B1 | 4/2003 | Vitek |
| 6,585,763 B1 | 7/2003 | Keilman et al. |
| 6,592,553 B2 | 7/2003 | Zhang et al. |
| 6,628,989 B1 | 9/2003 | Penner et al. |
| 6,660,021 B1 | 12/2003 | Palmer et al. |
| 6,685,638 B1 | 2/2004 | Taylor et al. |
| 6,699,186 B1 | 3/2004 | Wolinsky et al. |
| 6,702,847 B2 | 3/2004 | DiCarlo |
| 6,730,108 B2 | 5/2004 | Van Tassel et al. |
| 6,743,173 B2 | 6/2004 | Penner et al. |
| 6,746,404 B2 | 6/2004 | Schwartz |
| 6,747,916 B1 | 6/2004 | Fleury et al. |
| 6,755,855 B2 | 6/2004 | Yurek et al. |
| 6,764,446 B2 | 7/2004 | Wolinsky et al. |
| 6,783,499 B2 | 8/2004 | Schwartz |
| 6,840,956 B1 | 1/2005 | Wolinsky et al. |
| 6,855,115 B2 | 2/2005 | Fonseca et al. |
| 6,868,288 B2 | 3/2005 | Thompson |
| 6,890,303 B2 | 5/2005 | Fitz |
| 6,899,729 B1 | 5/2005 | Cox et al. |
| 6,920,347 B2 | 7/2005 | Simon et al. |
| 6,926,670 B2 | 8/2005 | Rich et al. |
| 6,970,742 B2 | 11/2005 | Mann et al. |
| 6,972,017 B2 | 12/2005 | Smith et al. |
| 7,006,858 B2 | 2/2006 | Silver et al. |
| 7,011,671 B2 | 3/2006 | Welch |
| 7,024,248 B2 | 4/2006 | Penner et al. |
| 7,035,684 B2 | 4/2006 | Lee |
| 7,060,038 B2 | 6/2006 | Letort et al. |
| 7,064,472 B2 | 6/2006 | Pelrine et al. |
| 7,083,822 B2 | 8/2006 | Brightbill |
| 7,118,531 B2 | 10/2006 | Krill |
| 7,131,986 B2 | 11/2006 | Sirhan et al. |
| 7,181,261 B2 | 2/2007 | Silver et al. |
| 7,198,603 B2 | 4/2007 | Penner et al. |
| 7,211,045 B2 | 5/2007 | Dala-Krishna et al. |
| 7,283,874 B2 | 10/2007 | Penner |
| 7,308,319 B2 | 12/2007 | Lovett et al. |
| 7,338,512 B2 | 3/2008 | McGuckin, Jr. et al. |
| 7,347,868 B2 | 3/2008 | Burnett et al. |
| 7,421,297 B2 | 9/2008 | Giftakis et al. |
| 7,452,334 B2 | 11/2008 | Gianchandani et al. |
| 7,460,906 B2 | 12/2008 | Libbus |
| 7,477,946 B2 | 1/2009 | Tockman et al. |
| 7,630,767 B1 | 12/2009 | Poore et al. |
| 7,765,000 B2 | 7/2010 | Zhang et al. |
| 7,780,694 B2 | 8/2010 | Palmer et al. |
| 7,850,708 B2 | 12/2010 | Pal |
| 7,890,185 B2 | 2/2011 | Cohen et al. |
| 8,571,653 B2 | 10/2013 | Ben-David et al. |
| 8,615,294 B2 | 12/2013 | Ben-David et al. |
| 8,634,912 B2 | 1/2014 | Bornzin et al. |
| 8,644,934 B2 | 2/2014 | Hastings et al. |
| 2002/0072656 A1 | 6/2002 | Vantassel et al. |
| 2002/0123672 A1 | 9/2002 | Christophersom et al. |
| 2002/0128546 A1 | 9/2002 | Silver |
| 2002/0165601 A1 | 11/2002 | Clerc |
| 2002/0183628 A1 | 12/2002 | Reich et al. |
| 2002/0188207 A1 | 12/2002 | Richter |
| 2003/0114897 A1 | 6/2003 | Von Arx |
| 2003/0139796 A1 | 7/2003 | Sequin et al. |
| 2003/0200031 A1 | 10/2003 | Kok |
| 2004/0006377 A1 | 1/2004 | Behm |
| 2004/0059392 A1 | 3/2004 | Parramon et al. |
| 2004/0116981 A1 | 6/2004 | Mazar |
| 2004/0116992 A1 | 6/2004 | Wardle et al. |
| 2004/0176672 A1 | 9/2004 | Silver et al. |
| 2004/0193229 A1 | 9/2004 | Starkebaum et al. |
| 2004/0204744 A1 | 10/2004 | Penner et al. |
| 2004/0215228 A1 | 10/2004 | Simpson et al. |
| 2005/0080472 A1 | 4/2005 | Atkinson et al. |
| 2005/0115561 A1 | 6/2005 | Stahmann et al. |
| 2005/0136385 A1 | 6/2005 | Mann et al. |
| 2005/0149108 A1 | 7/2005 | Cox |
| 2005/0149128 A1 | 7/2005 | Heil, Jr. et al. |
| 2005/0149155 A1 | 7/2005 | Scheiner et al. |
| 2005/0149156 A1 | 7/2005 | Libbus et al. |
| 2005/0154321 A1 | 7/2005 | Wolinsky et al. |
| 2005/0165456 A1 | 7/2005 | Mann et al. |
| 2005/0209678 A1 | 9/2005 | Henkes et al. |
| 2005/0245840 A1 | 11/2005 | Christopherson et al. |
| 2006/0004417 A1* | 1/2006 | Rossing ............ A61N 1/36114 607/9 |
| 2006/0009818 A1 | 1/2006 | Von Arx et al. |
| 2006/0047205 A1 | 3/2006 | Ludomirsky et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0079740 A1 | 4/2006 | Silver et al. |
| 2006/0089627 A1 | 4/2006 | Burnett et al. |
| 2006/0089694 A1 | 4/2006 | Zhang et al. |
| 2006/0122522 A1 | 6/2006 | Chavan et al. |

(56) References Cited

U.S. PATENT DOCUMENTS

| | | |
|---|---|---|
| 2006/0136004 A1 | 6/2006 | Cowan et al. |
| 2006/0142819 A1 | 6/2006 | Penner et al. |
| 2006/0149329 A1 | 7/2006 | Penner |
| 2006/0149330 A1 | 7/2006 | Mann et al. |
| 2006/0178586 A1 | 8/2006 | Dobak, III |
| 2006/0206153 A1 | 9/2006 | Libbus et al. |
| 2006/0241697 A1 | 10/2006 | Libbus et al. |
| 2006/0241735 A1 | 10/2006 | Tockman et al. |
| 2006/0259085 A1 | 11/2006 | Zhang et al. |
| 2006/0282145 A1 | 12/2006 | Caparso et al. |
| 2006/0287700 A1 | 12/2006 | White et al. |
| 2006/0293741 A1 | 12/2006 | Johnson et al. |
| 2007/0129637 A1 | 6/2007 | Wolinsky et al. |
| 2007/0156126 A1 | 7/2007 | Flaherty |
| 2007/0156205 A1 | 7/2007 | Larson et al. |
| 2007/0162090 A1 | 7/2007 | Penner |
| 2007/0179558 A1 | 8/2007 | Gliner et al. |
| 2007/0179583 A1 | 8/2007 | Goetzinger et al. |
| 2007/0191904 A1 | 8/2007 | Libbus et al. |
| 2007/0208390 A1 | 9/2007 | Von Arx et al. |
| 2007/0239243 A1 | 10/2007 | Moffitt et al. |
| 2007/0250126 A1 | 10/2007 | Maile et al. |
| 2007/0274565 A1 | 11/2007 | Penner |
| 2008/0021504 A1 | 1/2008 | McCabe et al. |
| 2008/0071178 A1 | 3/2008 | Greenland et al. |
| 2008/0071248 A1 | 3/2008 | Delgado et al. |
| 2008/0071339 A1 | 3/2008 | Stalker et al. |
| 2008/0086181 A1 | 4/2008 | Amurthur et al. |
| 2008/0086185 A1 | 4/2008 | Amurthur et al. |
| 2008/0108904 A1 | 5/2008 | Heil |
| 2008/0109045 A1 | 5/2008 | Gross et al. |
| 2008/0176271 A1 | 7/2008 | Silver et al. |
| 2008/0275350 A1 | 11/2008 | Liao et al. |
| 2008/0283066 A1 | 11/2008 | Delgado et al. |
| 2009/0054793 A1 | 2/2009 | Nunez et al. |
| 2009/0171274 A1 | 7/2009 | Harlev et al. |
| 2009/0270742 A1 | 10/2009 | Wolinsky et al. |
| 2010/0016840 A1 | 1/2010 | Stahmann et al. |
| 2010/0210923 A1 | 8/2010 | Li et al. |
| 2011/0071586 A1 | 3/2011 | Jacobson |
| 2012/0041508 A1* | 2/2012 | Rousso ................ A61N 1/025 607/37 |
| 2013/0150941 A1* | 6/2013 | Jadwizak ............... A61N 1/056 607/122 |
| 2014/0012344 A1 | 1/2014 | Hastings et al. |
| 2015/0088221 A1* | 3/2015 | Barr-Cohen ........... A61N 1/362 607/33 |

FOREIGN PATENT DOCUMENTS

| | | |
|---|---|---|
| EP | 1068836 | 1/2001 |
| EP | 1488735 | 6/2007 |
| GB | 2333044 | 7/1999 |
| JP | 11089942 | 4/1999 |
| JP | 2000507142 | 6/2000 |
| JP | 2001061790 | 3/2001 |
| WO | 8303348 | 10/1983 |
| WO | 9934731 | 7/1999 |
| WO | 0016686 | 3/2000 |
| WO | 0167989 | 9/2001 |
| WO | 0187137 | 11/2001 |
| WO | 2004024034 | 3/2004 |
| WO | 2005067817 | 7/2005 |
| WO | 2006062725 | 6/2006 |
| WO | 2007057739 | 5/2007 |
| WO | 2008034077 | 3/2008 |
| WO | 2008057720 | 5/2008 |
| WO | 2008060197 | 5/2008 |

OTHER PUBLICATIONS

Holmes et al (2006) Sirolimus-Eluting Stents vs Vascular Brachytherapy for In-Stent Restenosis Within Bare-Metal StentsThe SISR Randomized Trial Free.

Lanning et al (2003) Development and validation of implantable sensors for monitoring function of prosthetic heart valves:in vitro studies.

Sheth et al Subacute Thrombosis and Vascular Injury Resulting From Slotted-Tube Nitinol and Stainless Steel Stents in a Rabbit Carotid Artery Model.

Stone et al (2006) Paclitaxel-Eluting Stents vs Vascular Brachytherapy for In-Stent Restenosis Within Bare-Metal StentsThe TAXUS V ISR Randomized Trial Free.

Wenaweser et al (2005) Stent thrombosis following bare-metal stent implantation: success of emergency percutaneous coronary intervention and predictors of adverse outcome.

* cited by examiner

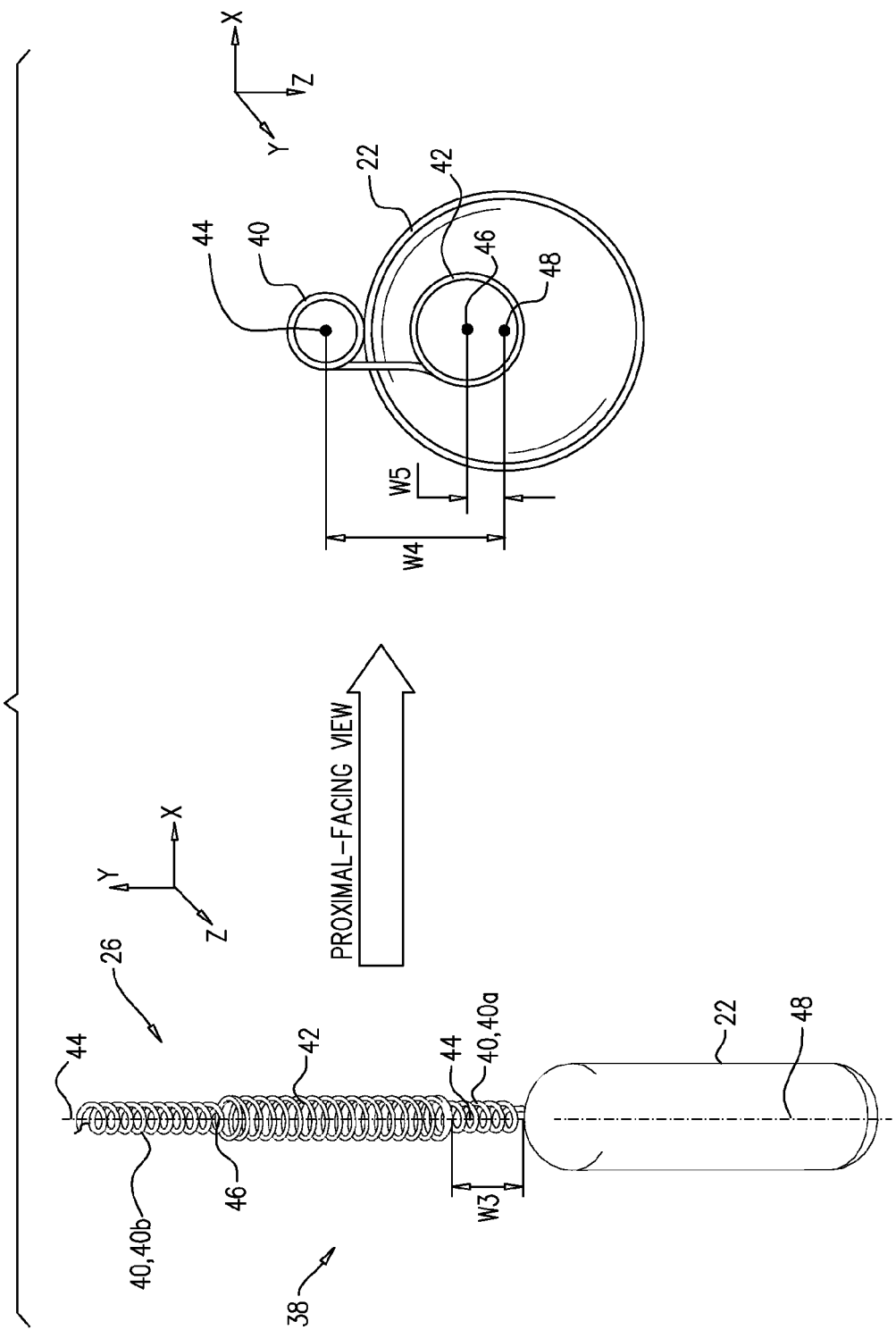

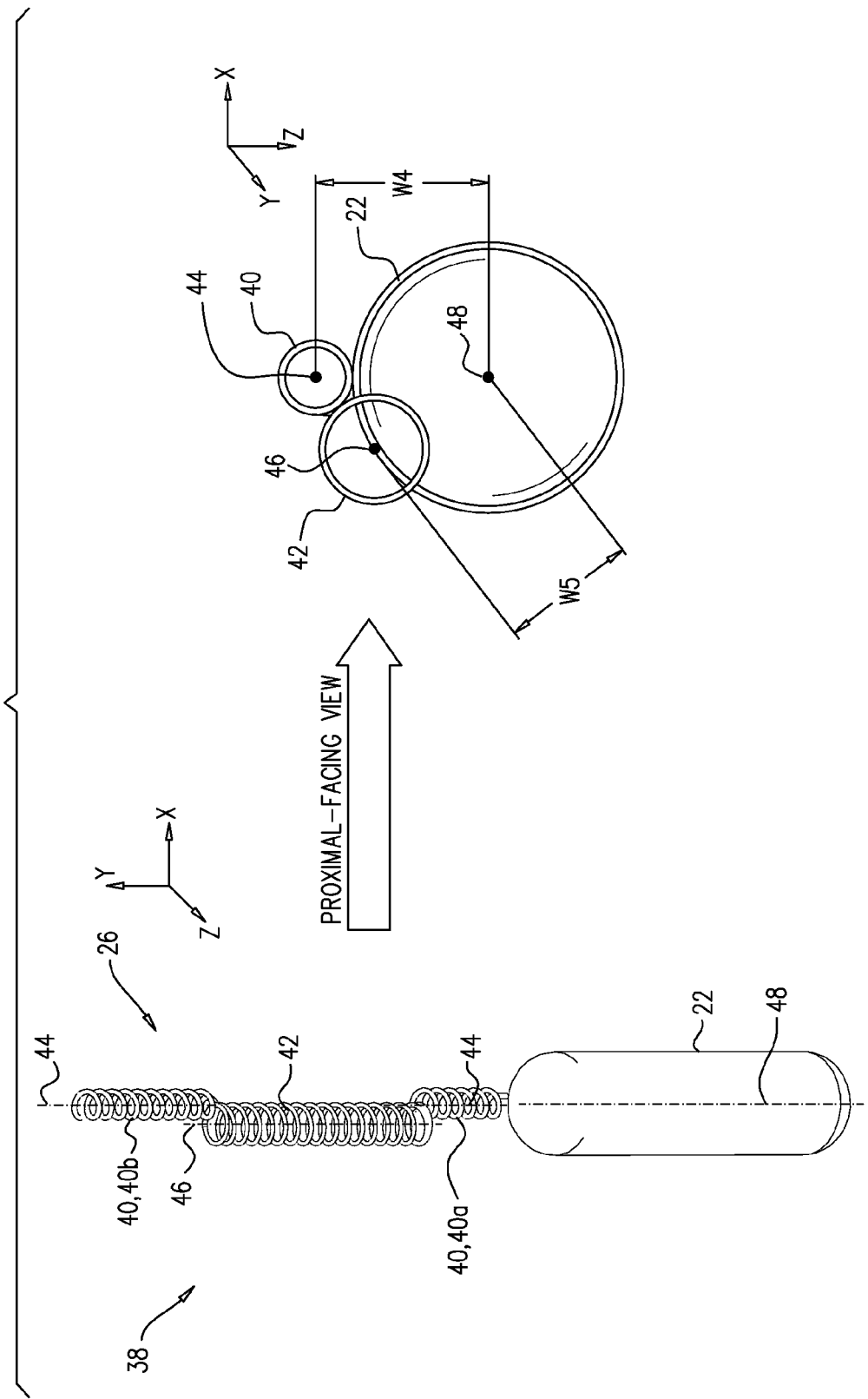

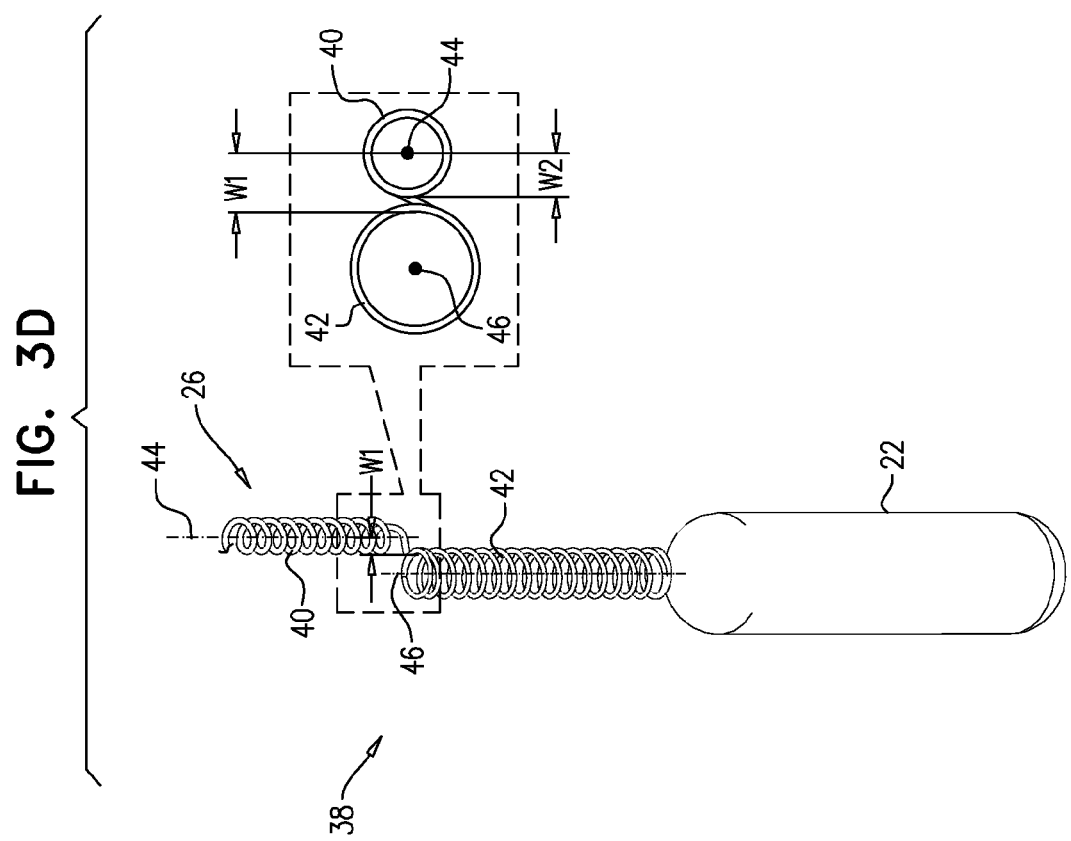

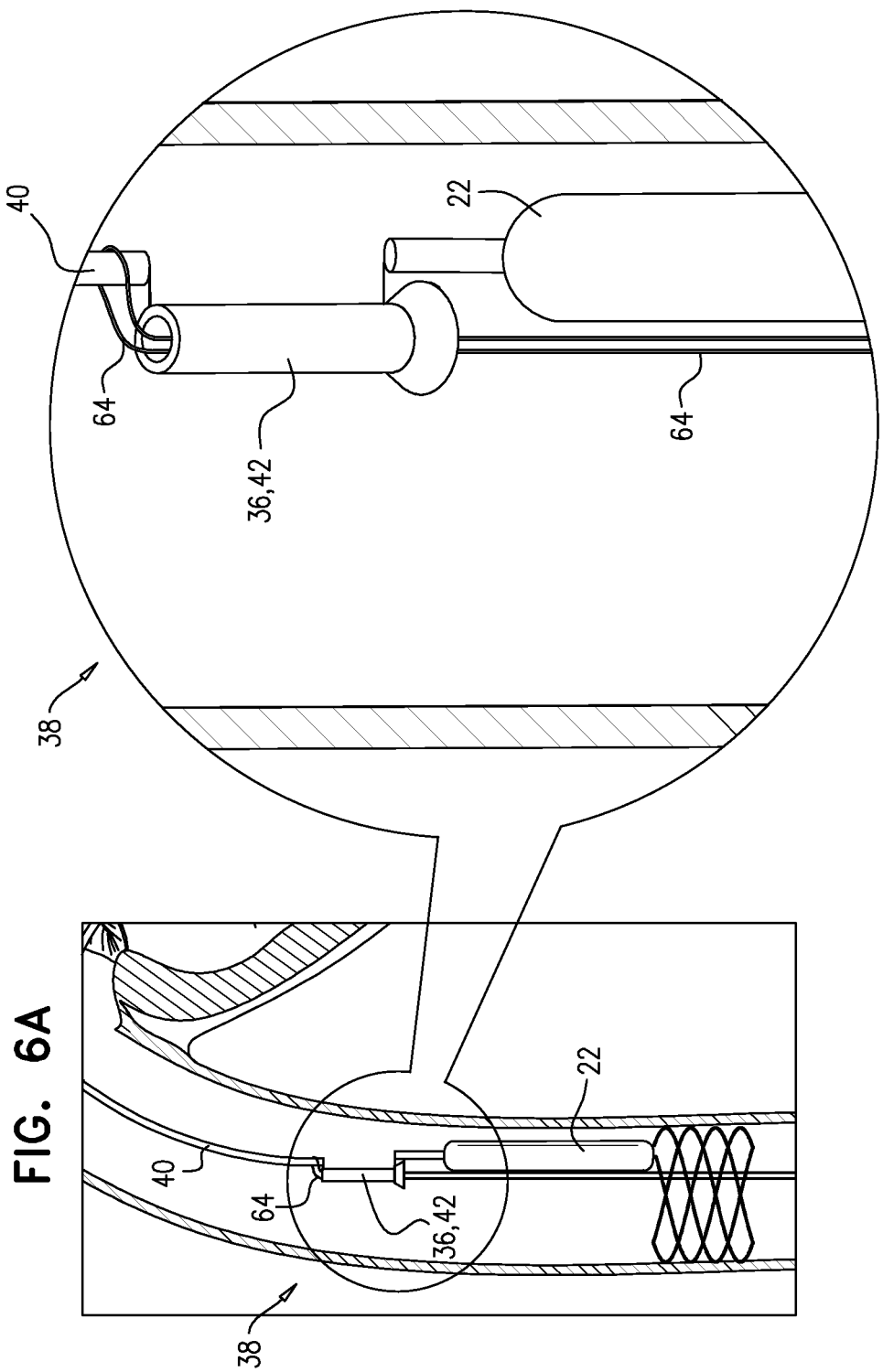

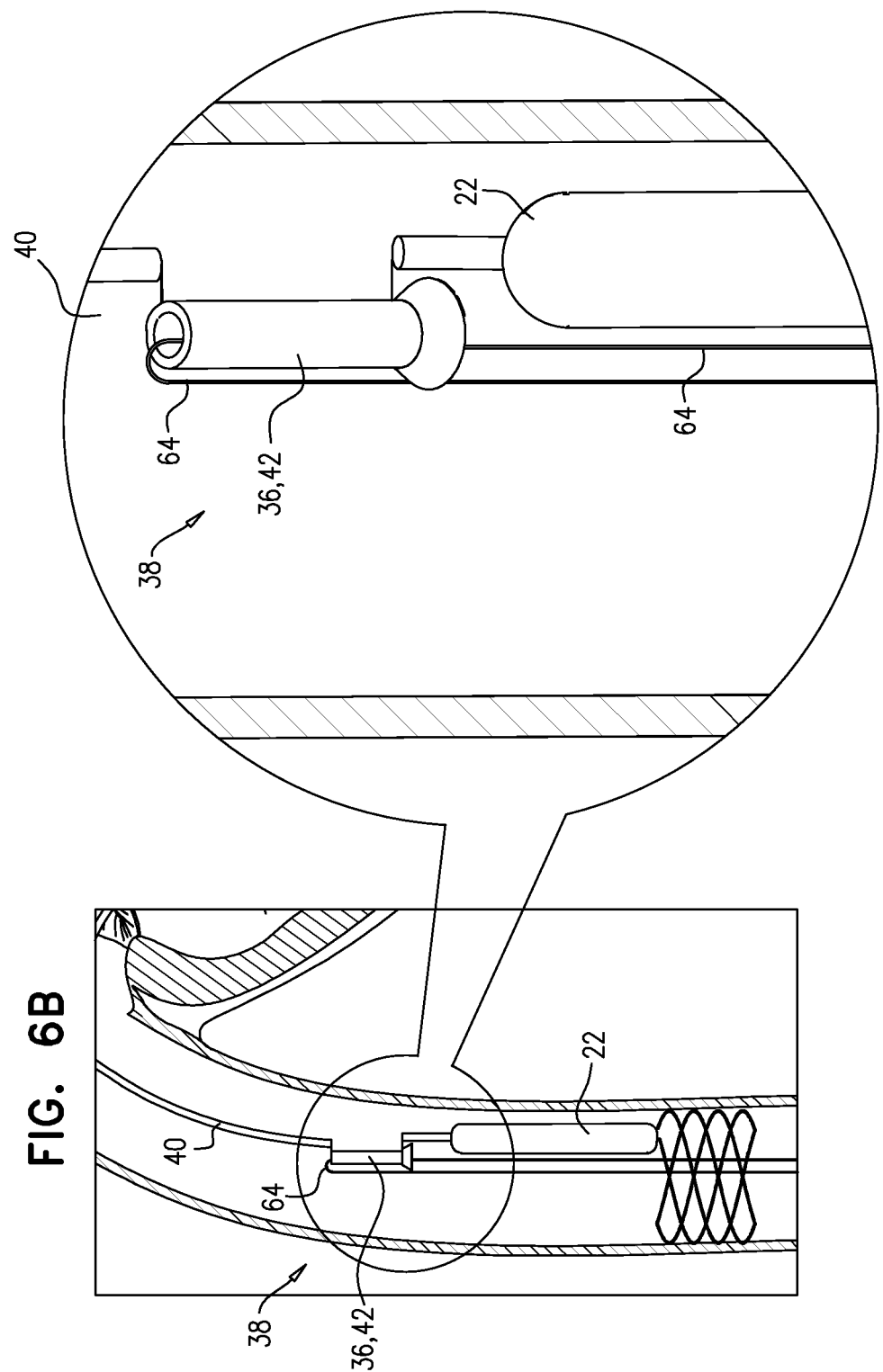

DUAL CHAMBER TRANSVENOUS PACEMAKER

FIELD OF THE INVENTION

Applications of the present invention relate to pacing a heart of a subject, particularly at multiple sites in the heart.

BACKGROUND

Some hearts require pacing at multiple sites. For example, some hearts require pacing of both a right atrium and a right ventricle.

SUMMARY OF THE INVENTION

Pacing a heart of a subject at multiple sites is typically challenging. In particular, when using a single implantable pulse generator (IPG) with multiple standard leads, it is typically difficult to choose an implantation location for the IPG, and/or lead lengths, such that each of the leads can reach its designated pacing site without leaving too much slack. When using multiple IPGs with standard leads, it is typically difficult to synchronize the pacing of the multiple sites.

Applications of the present invention include a method for implanting a first IPG and a second IPG in a subject, in order to facilitate pacing the subject's heart at two sites. The distal end of a first coiled lead, which is connected to the first IPG, is implanted at a first location in the subject's heart (e.g., in the right atrium), and subsequently, the first IPG is implanted in a blood vessel of the subject. Subsequently, the distal end of a second coiled lead, which is connected to the second IPG, is implanted at a second location in the subject's heart (e.g., in the right ventricle), and subsequently, the second IPG is implanted in the blood vessel. To facilitate synchronization between the IPGs, a portion of the second lead is aligned with respect to a portion of the first lead such that the central longitudinal axis of the portion of the second lead passes longitudinally through the portion of the first lead. For example, the portion of the second lead may be passed longitudinally through a portion of the first lead. Thus, a first pacing signal generated by one of the IPGs passes through one of the leads, and induces a synchronizing signal in the other one of the leads. The synchronizing signal is received by the other IPG, which then generates a second pacing signal in response to the synchronizing signal.

There is therefore provided, in accordance with some applications of the present invention, apparatus for pacing a heart of a subject, the apparatus including:

an implantable pulse generator (IPG); and
a coiled lead connected to the IPG, the coiled lead including:
  a smaller-diameter coiled portion, a lumen of which having a first coil-lumen-diameter, and
  a larger-diameter coiled portion electrically in series with the smaller-diameter coiled portion, a lumen of the larger-diameter coiled portion having a second coil-lumen-diameter that is larger than the first coil-lumen-diameter,
    a perpendicular distance from a central longitudinal axis of the smaller-diameter coiled portion to the lumen of the larger-diameter coiled portion being greater than an outer radius of the smaller-diameter coiled portion, when the central longitudinal axis of the smaller-diameter coiled portion is parallel to a central longitudinal axis of the larger-diameter coiled portion.

In some applications, a perpendicular distance between:
(a) a central longitudinal axis of the IPG and
(b) the central longitudinal axis of the smaller-diameter coiled portion
is greater than a perpendicular distance between:
(a) the central longitudinal axis of the IPG and
(b) the central longitudinal axis of the larger-diameter coiled portion,
when the central longitudinal axis of the IPG is parallel to (i) the central longitudinal axis of the larger-diameter coiled portion, and (ii) the central longitudinal axis of the smaller-diameter coiled portion.

In some applications, a longitudinal distance between the IPG and the larger-diameter coiled portion is at least 2 cm.

In some applications, a perpendicular distance between:
(a) a central longitudinal axis of the IPG and
(b) the central longitudinal axis of the larger-diameter coiled portion
is greater than a perpendicular distance between:
(a) the central longitudinal axis of the IPG and
(b) the central longitudinal axis of the smaller-diameter coiled portion,
when the central longitudinal axis of the IPG is parallel to (i) the central longitudinal axis of the larger-diameter coiled portion, and (ii) the central longitudinal axis of the smaller-diameter coiled portion.

In some applications,
(i) a central longitudinal axis of the IPG,
(ii) the central longitudinal axis of the smaller-diameter coiled portion, and
(iii) the central longitudinal axis of the larger-diameter coiled portion
are not all coplanar with each other.

In some applications, a perpendicular distance from a central longitudinal axis of the IPG to the lumen of the larger-diameter coiled portion is greater than an outer radius of the IPG, when the coiled lead is straight.

In some applications, a perpendicular distance from a central longitudinal axis of the IPG to the lumen of the smaller-diameter coiled portion is greater than an outer radius of the IPG, when the central longitudinal axis of the IPG is parallel to the central longitudinal axis of the smaller-diameter coiled portion.

In some applications, the IPG is shaped to define a channel, a proximal portion of the smaller-diameter coiled portion being disposed within the channel.

In some applications, a lateral wall of the IPG is shaped to define the channel.

In some applications, the channel is a lumen of the IPG.

In some applications, the smaller-diameter coiled portion is disposed between the IPG and the larger-diameter coiled portion.

In some applications,
the smaller-diameter coiled portion is a first smaller-diameter coiled portion,
the coiled lead further includes a second smaller-diameter coiled portion electrically in series with the larger-diameter coiled portion, a lumen of the second smaller-diameter coiled portion having a diameter that is less than the diameter of the lumen of the larger-diameter coiled portion,
the larger-diameter coiled portion is disposed between the first smaller-diameter coiled portion and the second smaller-diameter coiled portion, and a perpendicular distance from a central longitudinal axis of the second smaller-diameter coiled portion to the lumen of the larger-diameter coiled portion is greater than an outer radius of the second smaller-diameter coiled portion, when the central longitudinal axis of the second smaller-diameter coiled portion is parallel to the central longitudinal axis of the larger-diameter coiled portion.

In some applications, the larger-diameter coiled portion is disposed between the IPG and the smaller-diameter coiled portion.

In some applications, the apparatus further includes an intravascular stent, the IPG being coupled to the stent.

In some applications,
the IPG is a first IPG,
the coiled lead is a first coiled lead, and
the apparatus further includes:
  a second IPG that is not electrically or mechanically coupled to the first IPG;
  a second coiled lead connected to the second IPG, an outer diameter of the second coiled lead being less than the diameter of the lumen of the larger-diameter coiled portion; and
  a kit containing the first IPG, the first coiled lead, the second IPG, and the second coiled lead.

In some applications, an outer diameter of the second coiled lead is constant over at least 95% of a length of the second coiled lead.

In some applications, a length of the larger-diameter coiled portion of the first coiled lead is 0.5-5 cm.

In some applications, the length of the larger-diameter coiled portion of the first coiled lead is 1-3 cm.

In some applications, a proximal end of the larger-diameter coiled portion has a funnel-shaped configuration.

In some applications, the proximal end of the larger-diameter coiled portion is configured to have (i) a collapsed configuration when disposed inside of an enclosing lumen, and (ii) the funnel-shaped configuration when not disposed inside of the enclosing lumen.

In some applications, a distal end of the larger-diameter coiled portion is not funnel-shaped.

In some applications, the apparatus further includes a flexible longitudinal element passing through the larger-diameter coiled portion.

In some applications, the flexible longitudinal element is shaped as a loop.

In some applications, the flexible longitudinal element loops around the smaller-diameter coiled portion.

In some applications, the flexible longitudinal element passes through the larger-diameter coiled portion in a first direction, loops around the smaller-diameter coiled portion, and passes through the larger-diameter coiled portion in a second direction that is opposite the first direction.

There is further provided, in accordance with some applications of the present invention, apparatus for pacing a heart of a subject, the apparatus including:
  a first implantable pulse generator (IPG);
  a first coiled lead connected to the first IPG, a portion of the first coiled lead being shaped to define a first helix;
  a second implantable pulse generator (IPG); and
  a second coiled lead connected to the second IPG, a portion of the second coiled lead including a longitudinal element shaped to define a second helix,
    a pitch of the first helix being generally equal to a pitch of the second helix, when no longitudinal force is applied to the first helix and no longitudinal force is applied to the second helix.

In some applications, a space between consecutive turns of the first helix is between 0.5 and 1.5 times a diameter of the longitudinal element, when no longitudinal force is applied to the first helix.

There is further provided, in accordance with some applications of the present invention, a method for implanting a first implantable pulse generator (IPG) and a second IPG in a subject, the first IPG having a first coiled lead connected thereto, and the second IPG having a second coiled lead connected thereto, the method including:
  implanting a distal end of the first lead at a first location in a heart of the subject;
  subsequently to implanting the distal end of the first lead, implanting the first IPG in a blood vessel of the subject;
  subsequently to implanting the first IPG, implanting a distal end of the second lead at a second location in the heart of the subject;
  subsequently to implanting the distal end of the second lead, implanting the second IPG in the blood vessel of the subject; and
  aligning a portion of the second lead with respect to a portion of the first lead such that a central longitudinal axis of the portion of the second lead passes longitudinally through the portion of the first lead.

In some applications, aligning the portion of the second lead with respect to the portion of the first lead includes aligning the portion of the second lead with respect to the portion of the first lead before implanting the distal end of the second lead.

In some applications, aligning the portion of the second lead with respect to the portion of the first lead includes aligning the portion of the second lead with respect to the portion of the first lead after implanting the distal end of the second lead.

In some applications, aligning the portion of the second lead with respect to the portion of the first lead includes interdigitating helical turns of the second lead with helical turns of the first lead by laterally squeezing together the portion of the second lead with the portion of the first lead.

In some applications, laterally squeezing together the portion of the second lead with the portion of the first lead includes laterally squeezing together the portion of the second lead with the portion of the first lead by passing a hollow structure over the portion of the second lead and the portion of the first lead.

In some applications,
the portion of the first lead is a first proximal portion disposed proximally to the first IPG,
the portion of the second lead is a second proximal portion disposed proximally to the second IPG, and
the method includes laterally squeezing together the portion of the second lead with the portion of the first lead.

In some applications, the method further includes activating a locking mechanism that maintains the interdigitation of the helical turns of the second lead with the helical turns of the first lead.

In some applications, activating the locking mechanism includes activating a locking mechanism that cannot be deactivated without breaking the locking mechanism.

In some applications, the method further includes, by placing a sheath over the portion of the second lead and the portion of the first lead, maintaining the interdigitation of the helical turns of the second lead with the helical turns of the first lead.

In some applications, the method further includes, following the squeezing, inserting a ferrite core into a common lumen of the portion of the second lead and the portion of the first lead.

In some applications, the method further includes maintaining the interdigitation of the helical turns of the second lead with the helical turns of the first lead by inserting the ferrite core in the common lumen.

In some applications, aligning the portion of the second lead with respect to the portion of the first lead includes passing the portion of the second lead through the portion of the first lead.

In some applications, the method further includes inserting a ferrite core into a lumen of the second lead.

In some applications, passing the portion of the second lead through the portion of the first lead includes passing the portion of the second lead through the portion of the first lead by passing the portion of the second lead over a flexible longitudinal element that passes through the portion of the first lead.

In some applications, the method further includes, prior to passing the portion of the second lead through the portion of the first lead, passing the flexible longitudinal element through the portion of the first lead.

In some applications, passing the flexible longitudinal element through the portion of the first lead includes passing the flexible longitudinal element through the portion of the first lead in a first direction, and the method further includes passing the flexible longitudinal element in a second direction that is opposite the first direction.

In some applications, the method further includes, between the passing in the first direction and the passing in the second direction, looping the flexible longitudinal element around the first lead.

In some applications, the method further includes, following the passing of the portion of the second lead through the portion of the first lead, removing the flexible longitudinal element from the subject.

In some applications, the first location is a right atrium of the subject, and the second location is a right ventricle of the subject.

In some applications, implanting the distal end of the first lead includes using a tined anchor to anchor the distal end of the first lead in the right atrium, and implanting the distal end of the second lead includes using a screw anchor to anchor the distal end of the second lead in the right ventricle.

In some applications, the first location is a right ventricle of the subject, and the second location is a right atrium of the subject.

In some applications, implanting the first and second IPGs includes implanting the first and second IPGs in a vena cava of the subject.

There is further provided, in accordance with some applications of the present invention, a method for pacing a heart of a subject using a first implantable pulse generator (IPG) and a second IPG, the method including:

using the first IPG, transmitting a first pacing signal to the heart through a first coiled lead connected to the first IPG;

by transmitting the first pacing signal, inducing a synchronizing signal in a second coiled lead connected to the second IPG, a portion of the first coiled lead being aligned with respect to a portion of the second coiled lead such that a central longitudinal axis of one of the portions passes through another one of the portions; and using the second IPG:

receiving the synchronizing signal, and in response to the synchronizing signal, transmitting a second pacing signal to the heart.

There is further provided, in accordance with some applications of the present invention, a method for implanting medical apparatus in a subject, the medical apparatus including an implantable pulse generator (IPG), the method including:

implanting, at a sinoatrial node of the subject, a first lead that is connected to the IPG;

implanting, in a right ventricle of the subject, a second lead that is connected to the IPG; and implanting the IPG in a vena cava of the subject.

There is further provided, in accordance with some applications of the present invention, apparatus for pacing a heart of a subject, the apparatus including:

an implantable pulse generator (IPG);

a first lead connected to the IPG, the first lead including a longitudinal element coiled to define a first helix, the first helix being coiled to define a second helix; and a second lead connected to the IPG.

In some applications, the second lead includes a longitudinal element coiled to define a first helix, the first helix not being coiled to define a second helix.

In some applications, the apparatus further includes a screw anchor at a distal end of the first lead.

In some applications, the apparatus further includes a tined anchor at a distal end of the second lead.

There is further provided, in accordance with some applications of the present invention, a method for implanting medical apparatus in a subject, the medical apparatus including an implantable pulse generator (IPG), the method including:

implanting, at a first implantation location in a heart of the subject, a first lead that is connected to the IPG;

implanting, at a second implantation location in the heart of the subject, a second lead that is connected to the IPG;

following the implanting of the first lead, by moving the IPG to an IPG-implantation location in a blood vessel of the subject, changing a length of the first lead; and subsequently, implanting the IPG at the IPG-implantation location.

In some applications, moving the IPG to the IPG-implantation location includes moving the IPG to the IPG-implantation location following the implantation of the second lead.

In some applications, moving the IPG to the IPG-implantation location includes moving the IPG to the IPG-implantation location before implanting the second lead.

In some applications, implanting the first lead includes implanting the first lead by increasing a length of the first lead.

In some applications, implanting the first lead includes implanting the first lead in a right ventricle of the subject.

In some applications, implanting the second lead includes implanting the second lead in a right atrium of the subject.

In some applications, the first lead includes a longitudinal element coiled to define a first helix, the first helix being coiled to define a second helix, and changing the length of the first lead includes changing the length of the first lead by changing a length of the second helix.

In some applications, implanting the first lead includes implanting the first lead by turning a screw anchor disposed at a distal end of the first lead.

In some applications, turning the screw anchor includes using a stylet to turn the screw anchor.

In some applications, turning the screw anchor includes turning the screw anchor by rotating the IPG, the first lead, and the second lead around a central longitudinal axis of the first lead.

There is further provided, in accordance with some applications of the present invention, a method for implanting medical apparatus in a subject, the medical apparatus including an implantable pulse generator (IPG), the method including:

moving the IPG to an IPG-implantation location in a blood vessel of the subject;

implanting, at a first implantation location in a heart of the subject, a first lead that is connected to the IPG, by increasing a length of the first lead;

implanting, at a second implantation location in the heart of the subject, a second lead that is connected to the IPG; and subsequently, implanting the IPG at the IPG-implantation location.

In some applications, implanting the first lead includes implanting the first lead before implanting the second lead.

In some applications, implanting the first lead includes implanting the first lead after implanting the second lead.

In some applications, moving the IPG to the IPG-implantation location includes moving the IPG to the IPG-implantation location before implanting the first lead.

In some applications, the first lead includes a longitudinal element coiled to define a first helix, the first helix being coiled to define a second helix, and increasing the length of the first lead includes increasing the length of the first lead by increasing a length of the second helix.

In some applications, increasing the length of the second helix includes:

inserting a stylet into a lumen of the first helix; and increasing the length of the second helix by pushing with the stylet.

In some applications, the method further includes removing the stylet from the lumen of the first helix after implanting the first lead, and before implanting the second lead.

There is further provided, in accordance with some applications of the present invention, apparatus for implantation in a blood vessel of a subject, the apparatus including:

an intravascular stent shaped to define a socket; and an implantable pulse generator (IPG) shaped to define a bolt that is shaped to be secured by the socket.

In some applications, the bolt includes:

a bolt body shaped to be received by the socket; and a bolt cap shaped to inhibit release of the bolt from the socket.

There is further provided, in accordance with some applications of the present invention, a method including:

providing (a) an intravascular stent shaped to define a socket, and (b) an implantable pulse generator (IPG) shaped to define a bolt that is shaped to be secured by the socket; and coupling the IPG to the stent, by securing the bolt in the socket.

In some applications, securing the bolt in the socket includes securing the bolt in the socket by inserting the bolt into the socket from a direction that is substantially perpendicular to a central longitudinal axis of the bolt.

In some applications, inserting the bolt into the socket includes inserting the bolt into the socket by rotating the IPG around the central longitudinal axis of the bolt.

In some applications, the method further includes implanting the IPG in a blood vessel of a subject by expanding the stent, following the coupling of the IPG to the stent.

In some applications, coupling the IPG to the stent includes coupling the IPG to the stent while the stent is implanted in a blood vessel of a subject.

There is further provided, in accordance with some applications of the present invention, a method including:

inserting a tool into a blood vessel of a subject, the blood vessel containing:

an intravascular stent shaped to define a socket, and an implantable pulse generator (IPG) shaped to define a bolt, the IPG being coupled to the stent by the socket securing the bolt; and using the tool, uncoupling the IPG from the stent, by removing the bolt from the socket.

In some applications, removing the bolt from the socket includes removing the bolt from the socket by rotating the IPG around a central longitudinal axis of the bolt.

In some applications, removing the bolt from the socket includes removing the bolt from the socket by moving the bolt in a direction that is substantially perpendicular to a central longitudinal axis of the bolt.

In some applications, the method further includes recoupling the IPG to the stent by securing the bolt in the socket.

In some applications, the IPG is a first IPG, and the method further includes coupling a second IPG to the stent by securing a bolt of the second IPG in the socket.

The present invention will be more fully understood from the following detailed description of applications thereof, taken together with the drawings, in which:

BRIEF DESCRIPTION OF THE DRAWINGS

FIGS. 3A-D are schematic illustrations of apparatus for pacing a heart of a subject, in accordance with some applications of the present invention;

FIGS. 5 and 6A-B are schematic illustrations of apparatus for pacing a heart of a subject, in accordance with some applications of the present invention;

DETAILED DESCRIPTION OF APPLICATIONS

Figure 1:
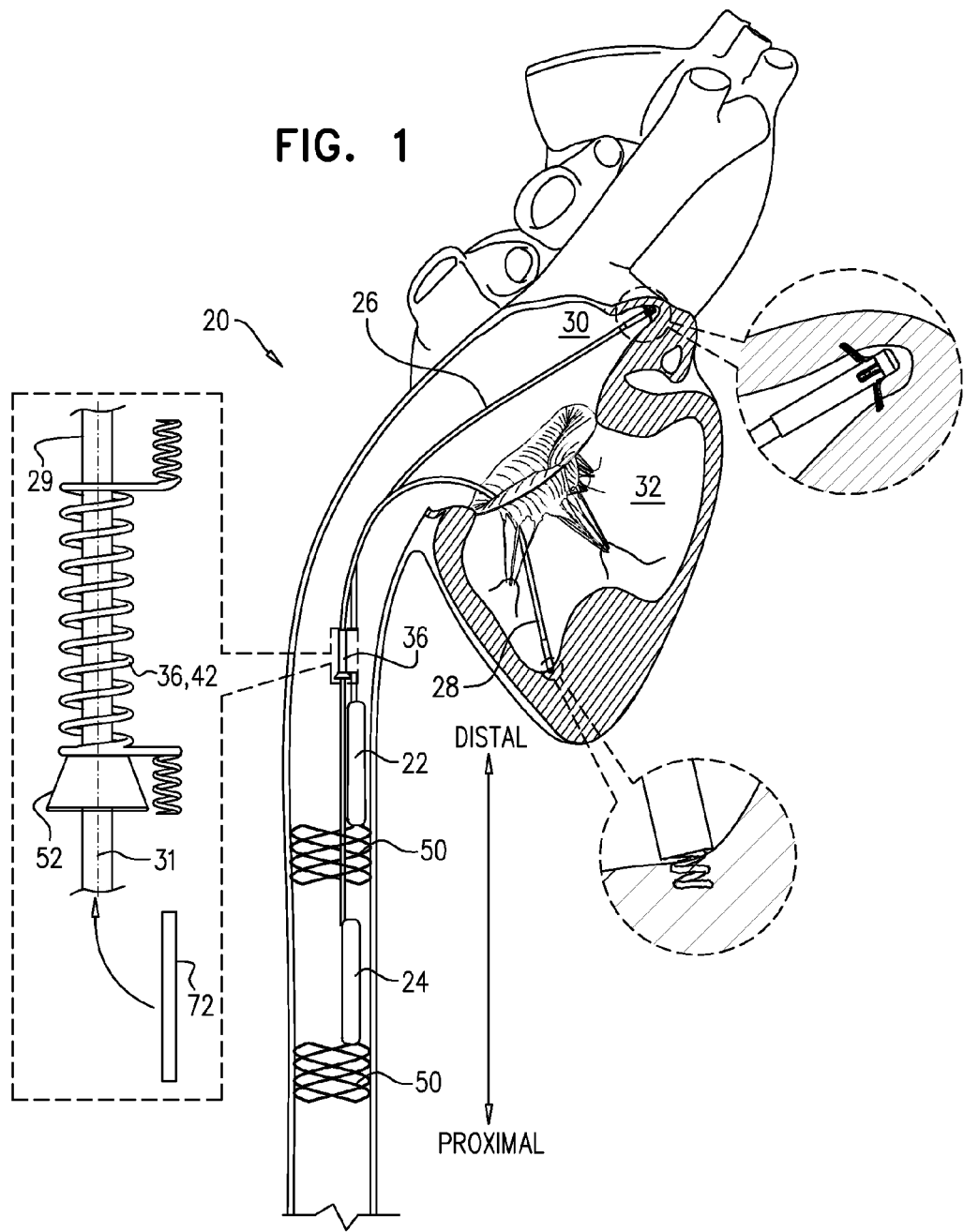
FIG. 1 is a schematic illustration of a method for implanting a first IPG and a second IPG in a subject, in accordance with some applications of the present invention.

Reference is made to FIG. 1, which is a schematic illustration of a method 20 for implanting a first IPG 22 and a second IPG 24 in a subject, in accordance with some applications of the present invention.

In method 20, the distal end of a first coiled lead 26, which is connected to first IPG 22, is implanted at a first location in the subject's heart, e.g., in the subject's right atrium 30. Subsequently to implanting the distal end of first lead 26, the first IPG is implanted in a blood vessel of the subject, e.g., in the subject's inferior vena cava or superior vena cava. Then, the distal end of a second coiled lead 28, which is connected to second IPG 24, is implanted at a second location in the subject's heart, e.g., in the subject's right ventricle 32, and subsequently, the second IPG is implanted in the blood vessel. Each of the IPGs is typically coupled to an intravascular stent 50, and is implanted by expanding stent 50.

To facilitate synchronization between the two IPGs, a portion 29 of the second lead is aligned with respect to a portion 36 of the first lead such that the central longitudinal axis 31 of the portion of the second lead passes longitudinally through portion 36. (In the context of the claims and specification of the present application, a "central longitudinal axis" of an elongate structure is the set of all centroids of cross-sectional sections of the structure along the structure, such that the cross-sectional sections are locally perpendicular to the central longitudinal axis, which runs along the structure.) For example, as shown in FIG. 1, portion 36 of the first lead may be a larger-diameter coiled portion 42 of the first lead. (That is, as further described hereinbelow with reference to FIGS. 3A-D, the lumen of portion 36 is "larger-diameter" in that the diameter of the lumen of portion 36 is greater than the diameter of the lumen of the other part of the lead.) In such applications, portion 29 of the second lead is aligned with respect to portion 36 by being passed through portion 36, before implanting the distal end of the second lead. In other applications, as described hereinbelow with respect to FIGS. 7-8, portion 29 is aligned with respect to portion 36 by being laterally squeezed together with portion 36. In such applications, the aligning may take place before or after the implantation of the distal end of the second lead.

It is noted that although, for illustrative purposes, the zoomed-in portion of FIG. 1 show the turns of first coiled lead 26 exposed, lead 26 is typically covered by a non-helical casing, as shown in the regular-size portion of the figure. Similarly, unless otherwise specified (e.g., as specified below with reference to FIGS. 7 and 8), it may be assumed that the various coils depicted in the figures are typically covered by a non-helical casing, such that the turns of the coil are not visible.

In some applications, to facilitate communication between the two leads, a ferrite core 72 is inserted into the lumen of the second lead. In particular, ferrite core 72 is typically inserted into the portion of the lumen that passes through portion 36 of the first lead. The insertion of the ferrite core may take place before or after the passing of the second lead through portion 36.

Following the implantation of the IPGs and the alignment of portions 29 and 36 with respect to each other, the two IPGs may operate in synch with respect to one another. In particular, using one of the IPGs, a first pacing signal may be transmitted to the heart through the coiled lead that is connected to the IPG. By transmitting the first pacing signal, a synchronizing signal is induced in the other coiled lead, due to the alignment of the leads with respect to one another. The synchronizing signal is received by the other IPG, which, in response to the synchronizing signal, transmits a second pacing signal to the heart.

For example, the first IPG may transmit a first pacing signal to the right atrium. As the first pacing signal passes through portion 36 of first lead 26, a synchronizing signal is induced in second lead 28. The synchronizing signal is received by the second IPG, which then transmits a second pacing signal to the right ventricle in response to the synchronizing signal. For example, the second IPG may transmit the second pacing signal a particular number of milliseconds following receipt of the synchronizing signal. (It is noted that although the synchronizing signal may also travel to the heart through the second lead, the synchronizing signal is typically not strong enough to pace the heart.) In general, a pacing signal from the second IPG may also induce a synchronizing signal that is received by the first IPG, i.e., communication between the IPGs may occur in either direction.

In some applications, as shown in FIG. 1, the proximal end 52 of the larger-diameter coiled portion has a funnel-shaped configuration. (In general, in the context of the specification and claims of the present application, the "proximal" and "distal" directions are with respect to the orifice through which the apparatus is inserted into the subject. For example, if the apparatus is deployed into the inferior vena cava as shown in FIG. 1, the proximal and distal directions are as depicted by the two-sided arrow in FIG. 1.) The funnel-shaped configuration of proximal end 52 facilitates the passing of the second lead through the larger-diameter coiled portion. Since the second lead is passed through the larger-diameter coiled portion from the proximal direction, there is typically no need for the distal end of the larger-diameter coiled portion to be funnel-shaped; thus, the distal end of the larger-diameter coiled portion is typically not funnel-shaped.

Figure 2:
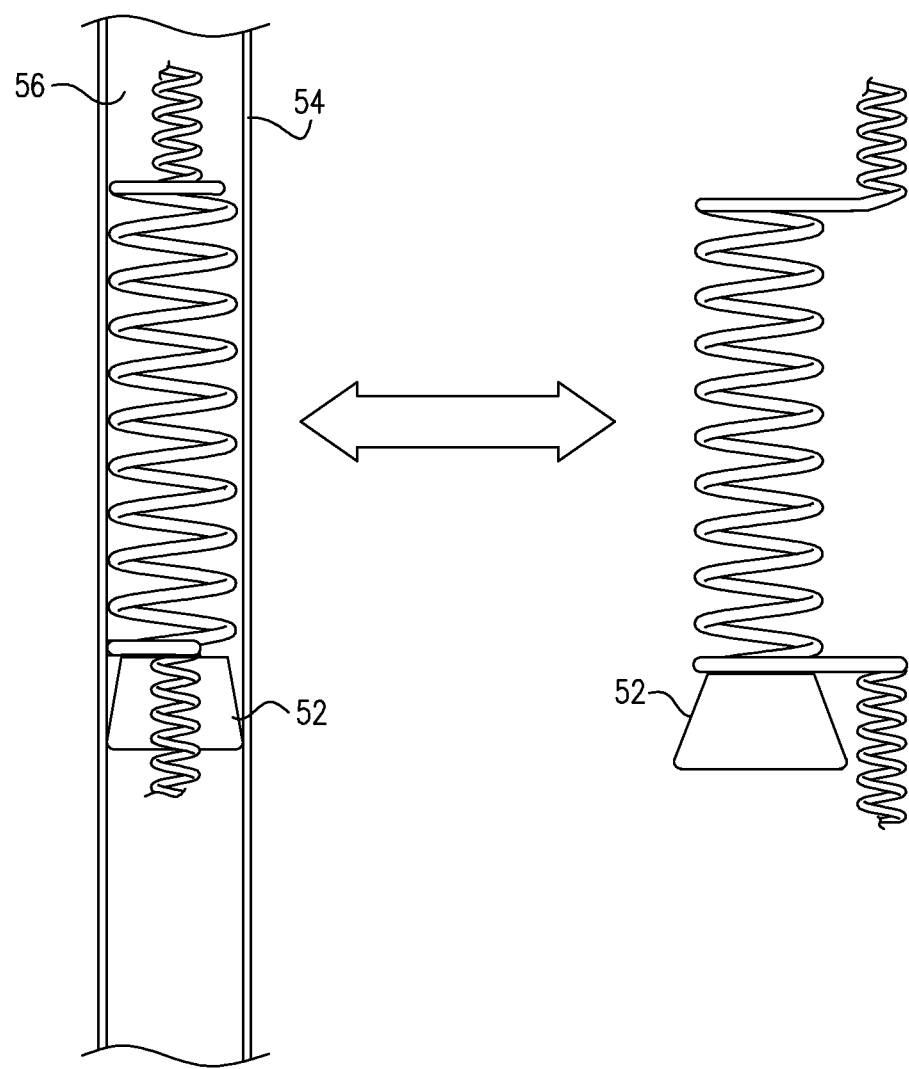
FIG. 2 is a schematic illustration of the proximal end of a larger-diameter coiled portion, in accordance with some applications of the present invention.

Reference is now made to FIG. 2, which is a schematic illustration of proximal end 52 of the larger-diameter coiled portion, in accordance with some applications of the present invention. Typically, to facilitate the delivery of the apparatus, proximal end 52 of the larger-diameter coiled portion is configured to have (i) a collapsed configuration when disposed inside of an enclosing lumen 56 (e.g., the lumen of a delivery catheter 54), and (ii) the funnel-shaped configuration when not disposed inside of enclosing lumen 56.

Figure 3A:
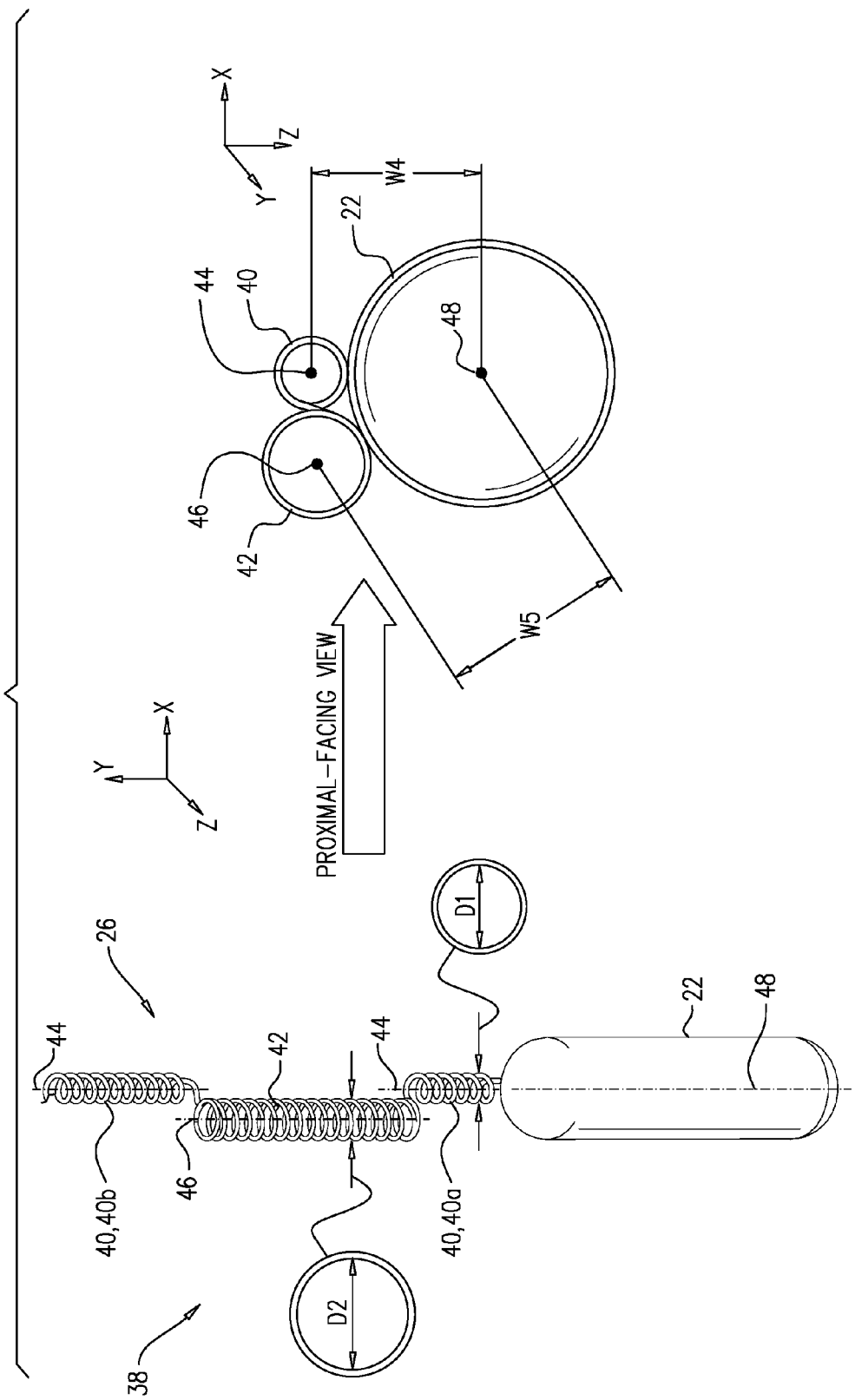

Reference is now made to FIGS. 3A-D, which are schematic illustrations of apparatus 38 for pacing a heart of a subject, in accordance with some applications of the present invention. Apparatus 38 comprises an IPG, corresponding to first IPG 22 of FIG. 1. Apparatus 38 further comprises a coiled lead connected to the IPG, the coiled lead corresponding to first coiled lead 26 of FIG. 1. Coiled lead 26 comprises (i) a smaller-diameter coiled portion 40, and (ii) a larger-diameter coiled portion 42 electrically in series with the smaller-diameter coiled portion. Smaller-diameter coiled portion 40 is "smaller-diameter" in that the diameter of its lumen is less than the diameter of the lumen of the larger-diameter coiled portion. In other words, as shown in FIG. 3A, the lumen of the smaller-diameter coiled portion has a first coil-lumen-diameter D1, and the lumen of the larger-diameter coiled portion has a second coil-lumen-diameter D2 that is larger than D1. Second coiled lead 28 (FIG. 1), which is connected to the second IPG, has an outer diameter that is less than D2; hence, as described hereinabove with reference to FIG. 1, the second lead may be passed longitudinally through the larger-diameter coiled portion, to facilitate communication between the two IPGs.

In some applications, as shown in FIGS. 3A-C, the smaller-diameter coiled portion is disposed between the IPG and the larger-diameter coiled portion. For example, coiled lead 26 may comprise two smaller-diameter coiled portions 40a and 40b, portion 40a being disposed between the IPG and larger-diameter coiled portion 42, and the larger-diameter coiled portion being disposed between portions 40a and 40b. (Each of portions 40a and 40b is electrically in series with the larger-diameter coiled portion.) In other applications, as shown in FIG. 3D, larger-diameter coiled portion 42 is disposed between the IPG and smaller-diameter coiled portion 40.

By way of introduction to the following description of FIGS. 3A-D, it is noted that applications of the present invention generally manage the following two design constraints:

(i) To facilitate implantation of the first lead, a stylet is typically inserted into the lumen of the smaller-diameter coiled portion. Hence, neither the IPG nor the larger-diameter coiled portion should inhibit access to the lumen of the smaller-diameter coiled portion.

(ii) To facilitate passing the second lead through the larger-diameter coiled portion, the IPG and the smaller-diameter coiled portion should not inhibit access to the larger-diameter coiled portion.

In general, the applications of FIGS. 3A-C satisfy the first constraint by laterally offsetting the smaller-diameter coiled portion from the IPG and from the larger-diameter coiled portion. The offset from the IPG is shown as being along the Z-axis, such that the smaller-diameter coiled portion is shown as being disposed "behind" the IPG. FIGS. 3A-C differ from each other mainly in the manner in which the larger-diameter coiled portion is laterally offset from the smaller-diameter coiled portion and/or the IPG. In particular:

(i) In FIG. 3A, the larger-diameter coiled portion is offset from the smaller-diameter coiled portion along the X-axis, such that the central longitudinal axis 48 of the IPG, central longitudinal axis 44 of the smaller-diameter coiled portion, and central longitudinal axis 46 of the larger-diameter coiled portion are not all coplanar with each other. (Hence, in the proximal-facing view of FIG. 3A, the three central longitudinal axes constitute the three vertices of a triangle.) Since the larger-diameter coiled portion is laterally offset from the IPG, the longitudinal distance between the IPG and the larger-diameter coiled portion may be relatively small. (In other words, significant longitudinal separation between the IPG and the larger-diameter coiled portion may not be necessary, since the lateral separation between the larger-diameter coiled portion and the IPG may already allow access to the lumen of the larger-diameter coiled portion.)

(ii) In FIG. 3B, the larger-diameter coiled portion is laterally offset from the smaller-diameter coiled portion along the Z-axis, such that the three central longitudinal axes are generally coplanar with each other. (Hence, in the proximal-facing view of FIG. 3B, the three central longitudinal axes generally constitute three points on a line.) To help limit the amount of space within the blood vessel occupied by the apparatus, the larger-diameter coiled portion is typically offset along the Z-axis toward the IPG, as shown in FIG. 3B, rather than away from the IPG. Hence, in order to facilitate access of the second lead to the lumen of the larger-diameter coiled portion, the larger-diameter coiled portion is typically longitudinally offset from the IPG by at least 2 cm, i.e., the longitudinal distance W3 between the IPG and the larger-diameter coiled portion is typically at least 2 cm.

As further shown in FIG. 3B, due to the offset of the larger-diameter coiled portion toward the IPG, the perpendicular distance W4 between central longitudinal axis 48 of the IPG and central longitudinal axis 44 of the smaller-diameter coiled portion is greater than the perpendicular distance W5 between central longitudinal axis 48 of the IPG and central longitudinal axis 46 of the larger-diameter coiled portion, when central longitudinal axes 44, 46, and 48 are parallel to each other. In FIG. 3A, on the other hand, distance W5 is greater than distance W4, i.e., central longitudinal axis 46 of the larger-diameter coiled portion is further from central longitudinal axis 48 of the IPG than is central longitudinal axis 44 of the smaller-diameter coiled portion.

(iii) FIG. 3C shows a "hybrid" of FIGS. 3A and 3B, whereby the larger-diameter coiled portion is offset from the smaller-diameter coiled portion along both the X- and Z-axes. As in FIG. 3A, the three central longitudinal axes are not coplanar with each other, yet, as in FIG. 3B, distance W4 between central longitudinal axis 48 of the IPG and central longitudinal axis 44 of the smaller-diameter coiled portion is greater than distance W5 between central longitudinal axis 48 of the IPG and central longitudinal axis 46 of the larger-diameter coiled portion, when central longitudinal axes 44, 46, and 48 are parallel to each other.

In the application shown in FIG. 3D, the larger-diameter coiled portion is laterally offset from both the IPG and the smaller-diameter coiled portion, while the smaller-diameter coiled portion may be laterally and/or longitudinally offset from the IPG. FIG. 3D shows the larger-diameter coiled portion being laterally offset from the smaller-diameter coiled portion, such that neither one of the portions inhibits access to the lumen of the other one of the portions. In particular, FIG. 3D shows (a) W1 as being the perpendicular distance from central longitudinal axis 44 of the smaller-diameter coiled portion to the lumen of the larger-diameter coiled portion, and (b) W2 as being the outer radius of the smaller-diameter coiled portion. When central longitudinal axis 44 of the smaller-diameter coiled portion is parallel to central longitudinal axis 46 of the larger-diameter coiled portion, W1 is greater than W2, i.e., the larger-diameter coiled portion is sufficiently offset from the smaller-diameter coiled portion such that the lumen of the larger-diameter coiled portion is not blocked by the smaller-diameter coiled portion. Similarly, the perpendicular distance from central longitudinal axis 46 of the larger-diameter coiled portion to the lumen of the smaller-diameter coiled portion is greater than the outer radius of the larger-diameter coiled portion, i.e., the lumen of the smaller-diameter coiled portion is not blocked by the larger-diameter coiled portion.

The concept of "sufficient lateral offset," as illustrated in FIG. 3D, applies also to FIGS. 3A-C. In particular, in FIGS.

3A-C, the larger-diameter coiled portion is sufficiently laterally offset from both of smaller-diameter coiled portions 40a and 40b. In other words, for each of the smaller-diameter coiled portions, the perpendicular distance from the central longitudinal axis of the smaller-diameter coiled portion to the lumen of the larger-diameter coiled portion is greater than the outer radius of the smaller-diameter coiled portion, when the central longitudinal axis of the smaller-diameter coiled portion is parallel to the central longitudinal axis of the larger-diameter coiled portion, i.e., neither one of the smaller-diameter coiled portions blocks the lumen of the larger-diameter coiled portion. (Similarly, the larger-diameter coiled portion does not block the lumen of either one of the smaller-diameter coiled portions.)

In FIGS. 3A-C, the smaller-diameter coiled portion (and in particular, portion 40a, which is adjacent to the IPG) is laterally offset from the IPG. That is, the perpendicular distance from the central, longitudinal axis of the IPG to the lumen of the smaller-diameter coiled portion is greater than the outer radius of the IPG, when the central longitudinal axis of the IPG is parallel to the central longitudinal axis of the smaller-diameter coiled portion. In FIG. 3D, where the smaller-diameter coiled portion is longitudinally offset from the IPG, the smaller-diameter coiled portion may not necessarily be laterally offset from the IPG.

Reference is now made to FIGS. 4A-D, which show lateral offsets of the smaller-diameter coiled portion, larger-diameter coiled portion, and IPG with respect to each other, in accordance with some applications of the present invention.

Figure 4A:
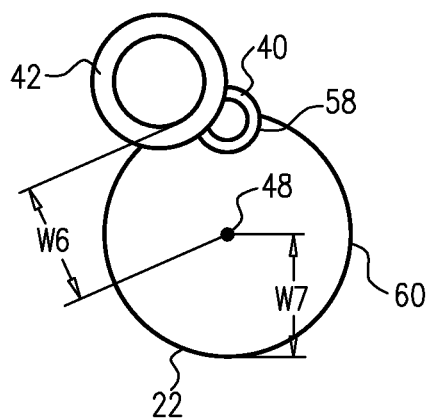
FIGS. 4A-D show lateral offsets of a smaller-diameter coiled portion, a larger-diameter coiled portion, and an IPG with respect to each other, in accordance with some applications of the present invention.
Figure 4B:
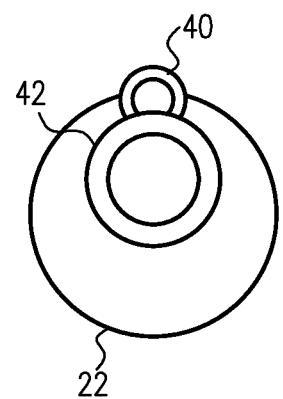
Figure 4C:
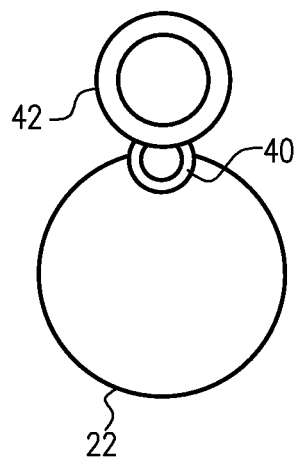
Figure 4D:
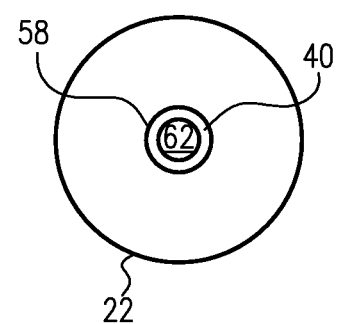

FIG. 4A roughly corresponds to the proximal-facing view of FIG. 3A. In FIG. 4A, the lateral offset of the larger-diameter coiled portion from the IPG is explicitly marked. In particular, FIG. 4A shows (a) W6 as being the perpendicular distance from central longitudinal axis 48 of the IPG to the lumen of the larger-diameter coiled portion, and (b) W7 as being the outer radius of the IPG. When the coiled lead is straight, W6 is greater than W7, such that the IPG does not block the lumen of the larger-diameter coiled portion. FIG. 4B roughly corresponds to the proximal-facing view of FIG. 3B, while FIG. 4C corresponds to an application in which the larger-diameter coiled portion is offset along the Z-axis away from the IPG. FIG. 4D generally does not correspond to any of the previous figures, and is described immediately below.

In some applications, the IPG is shaped to define a channel 58, a proximal portion of the smaller-diameter coiled portion being disposed within channel 58. For example, as shown in FIGS. 4A-C, the lateral wall 60 of the IPG may be shaped to define the channel. In some applications, as shown in FIG. 4D, the channel is a lumen 62 of the IPG. (The larger-diameter coiled portion is not shown in FIG. 4D.) The channel generally allows the smaller-diameter coiled portion to be disposed close to the IPG, without the IPG blocking the lumen of the smaller-diameter coiled portion. Thus, channel 58 helps reduce the space that is occupied by the apparatus within the blood vessel.

Figure 5:
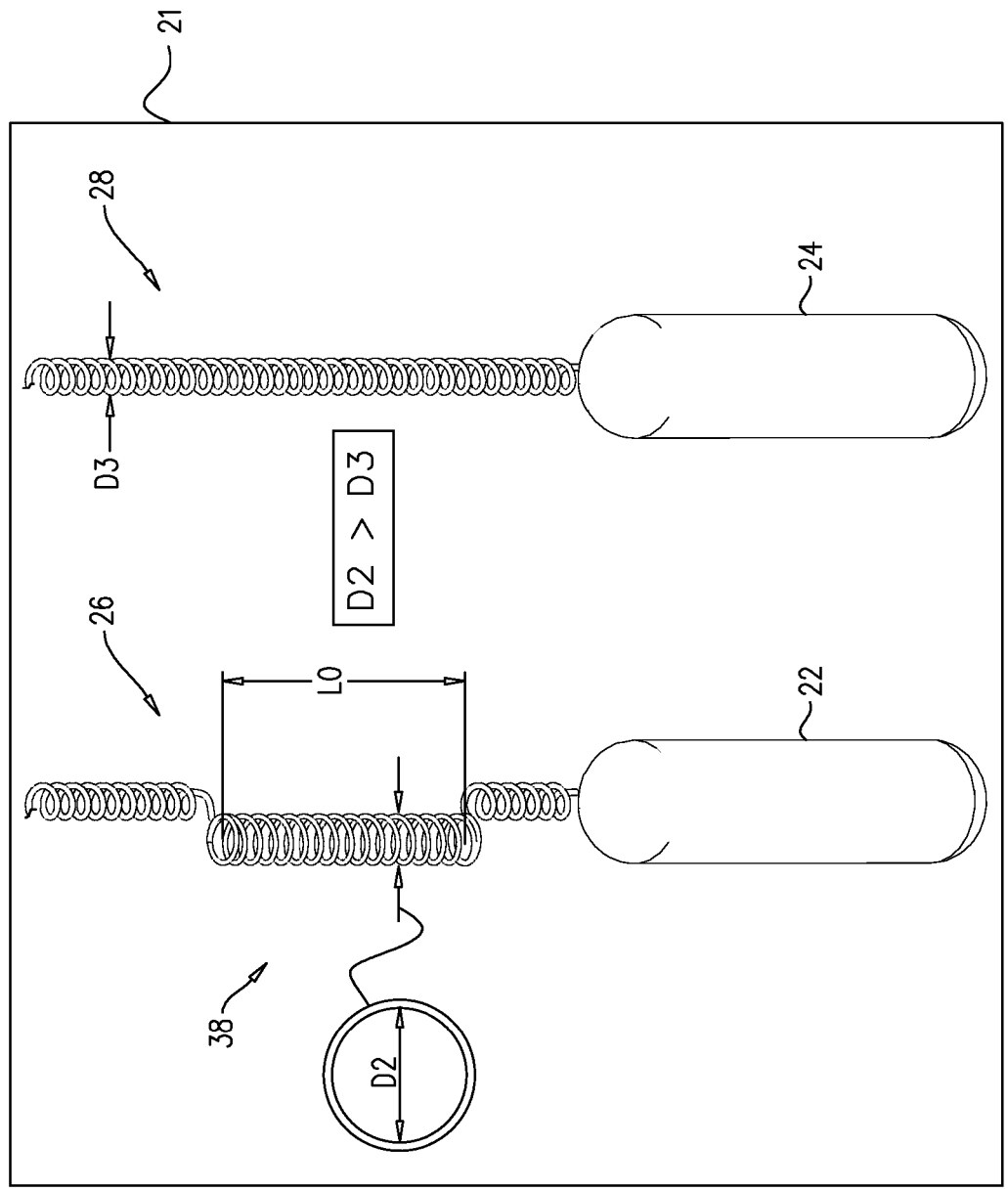

Reference is now made to FIG. 5, which is a schematic illustration of apparatus 38, in accordance with some applications of the present invention. Typically, apparatus 38 comprises a kit 21 containing first IPG 22, second IPG 24, first coiled lead 26, and second coiled lead 28. Second IPG 24 is not electrically or mechanically coupled to the first IPG, when contained inside kit 21.

Typically, the length L0 of the larger-diameter coiled portion of the first coiled lead is at least 0.5 cm and/or less than 5 cm, e.g., between 1 and 3 cm. In contrast to the non-constant diameter of the first coiled lead, the diameter of the second coiled lead is typically generally constant. For example, the outer diameter D3 of the second coiled lead may be constant over at least 95% (e.g., substantially all) of the length of the second coiled lead. As noted above with reference to FIG. 3A, diameter D2 of the lumen of the larger-diameter coiled portion is greater than D3, such that the second coiled lead may be passed through the larger-diameter coiled portion.

Reference is now made to FIGS. 6A-B, which are schematic illustrations of apparatus 38, in accordance with some applications of the present invention. In some applications, apparatus 38 further comprises a flexible longitudinal element 64 (e.g., a suture) passing through portion 36 (e.g., larger-diameter coiled portion 42) of the first lead. (Alternatively, during the procedure and prior to passing the second lead through portion 36, the flexible longitudinal element is passed through portion 36.) In such applications, the second lead is passed through the larger-diameter coiled portion by being passed over the flexible longitudinal element, i.e., the flexible longitudinal element is used as a guidewire. Following the passing of the second lead through the larger-diameter coiled portion, the flexible longitudinal element is removed from the subject.

In some applications, as shown in FIGS. 6A-B, the flexible longitudinal element is shaped as a loop. For example, as shown in FIG. 6A, the flexible longitudinal element may loop around the smaller-diameter coiled portion. In some applications, as further shown in FIG. 6A, the flexible longitudinal element passes through the larger-diameter coiled portion in a first direction, loops around the smaller-diameter coiled portion, and passes through the larger-diameter coiled portion in a second direction that is opposite the first direction. In general, the loop shape of the flexible longitudinal element helps the physician ascertain that the second lead has passed through the larger-diameter coiled portion, since the physician feels some resistance as the second lead reaches the distal end of the loop.

As noted above, in some applications, the flexible longitudinal element is passed through the larger-diameter coiled portion during the procedure, prior to passing the second lead through the larger-diameter coiled portion. In such applications, the flexible longitudinal element may be passed through the larger-diameter coiled portion such that the flexible longitudinal element has the loop shape described above, i.e., the flexible longitudinal element may be passed through the larger-diameter coiled portion in a first direction, and also passed in a second direction that is opposite the first direction. For example, the flexible longitudinal element may be passed (i) distally through the larger-diameter coiled portion, and (ii) proximally through (as in FIG. 6A) or next to (as in FIG. 6B) the larger-diameter coiled portion. Alternatively, the flexible longitudinal element may be passed (i) distally through (as in FIG. 6A) or next to (as in FIG. 6B) the larger-diameter coiled portion, and (ii) proximally through the larger-diameter coiled portion. Temporally between the passing in the first direction and the passing in the second direction, the flexible longitudinal element may be looped around the first lead, as in FIG. 6A.

Figure 7:
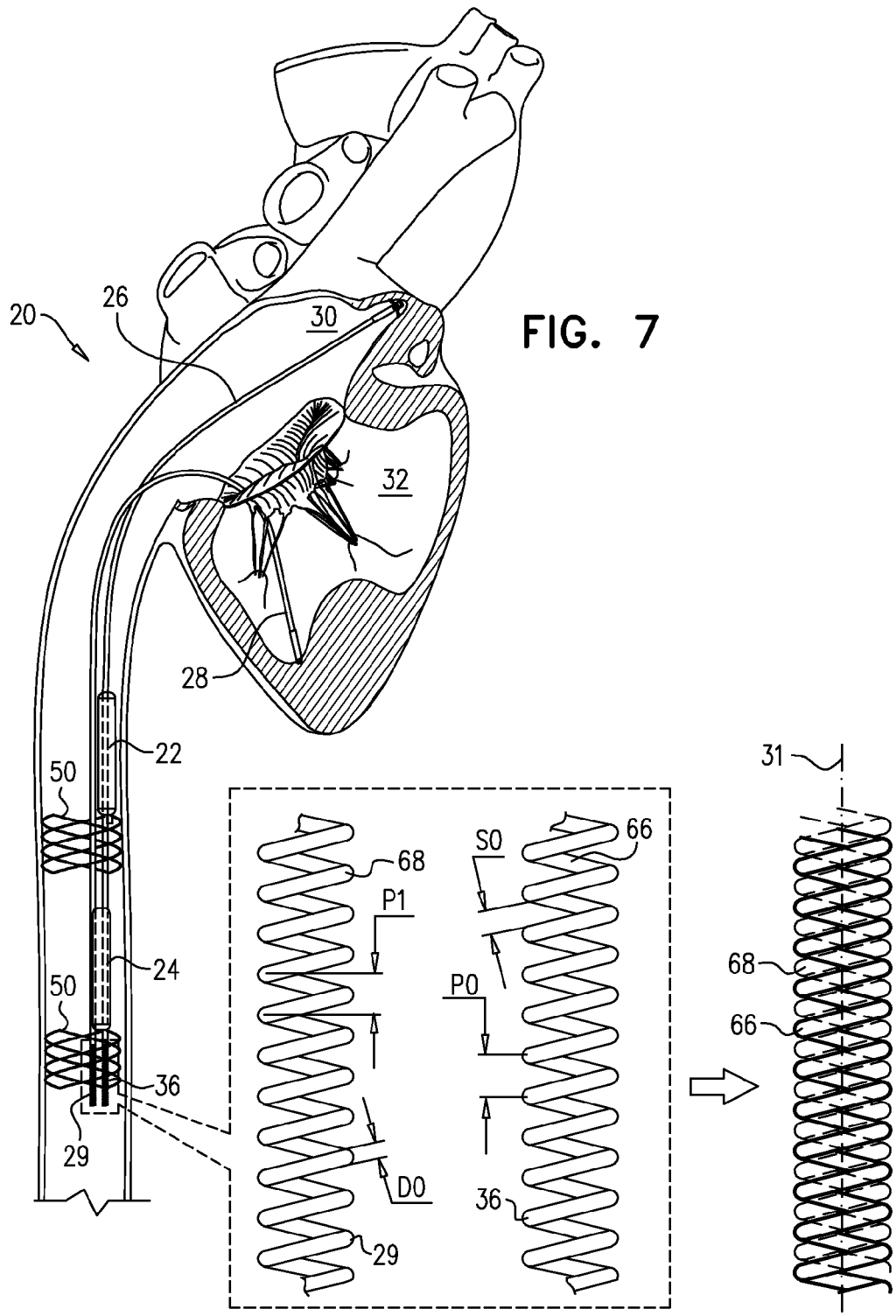
FIG. 7 is a schematic illustration of a method for implanting a first IPG and a second IPG in a subject, in accordance with some applications of the present invention.
Figure 8:
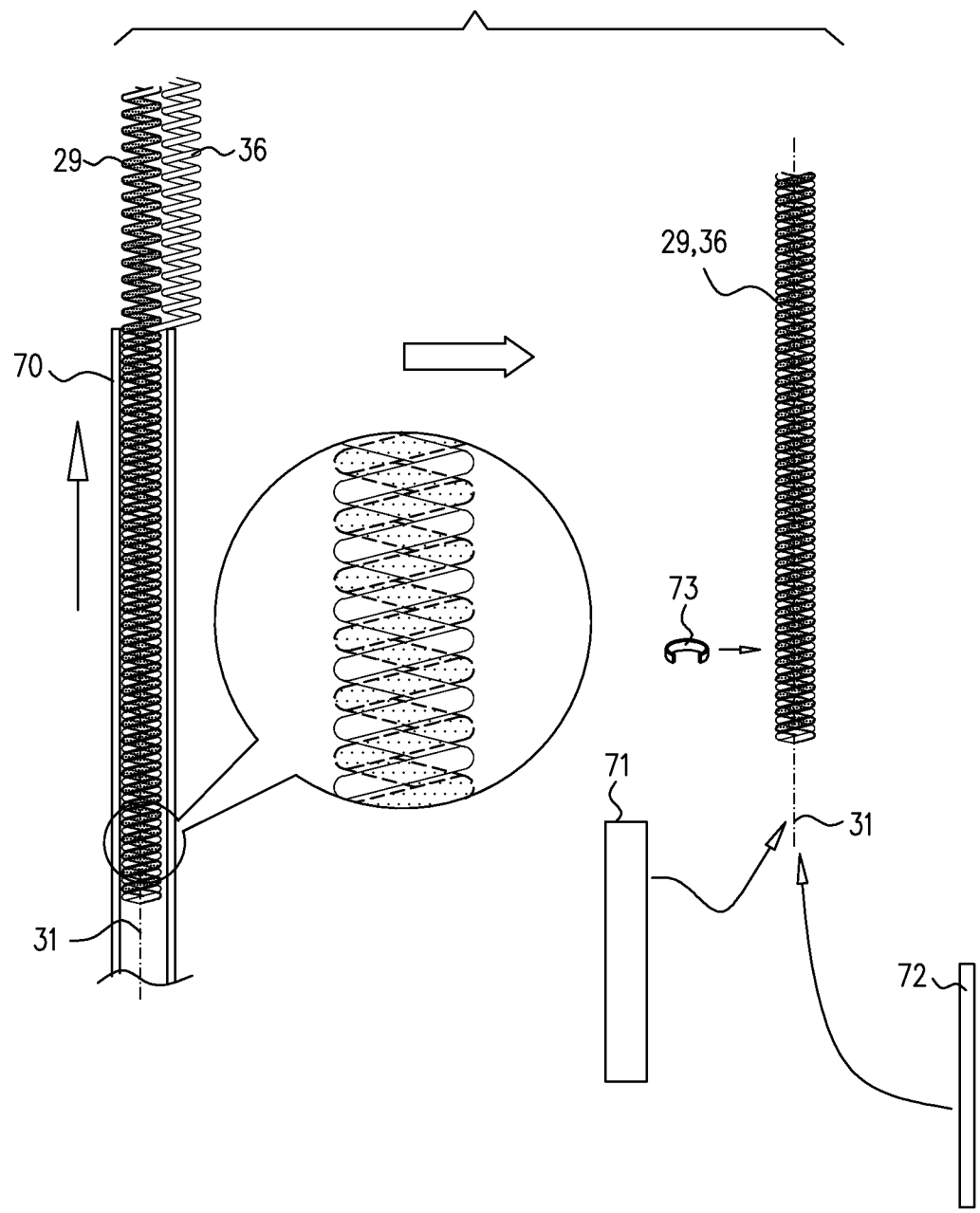
FIG. 8 is a schematic illustration of a technique for lateral squeezing, in accordance with some applications of the present invention.

Reference is now made to FIG. 7, which is a schematic illustration of method 20, in accordance with some applications of the present invention. Reference is also made to FIG. 8, which is a schematic illustration of a technique for lateral squeezing, in accordance with some applications of the present invention.

In some applications, portion 36 of first coiled lead 26 is shaped to define a first helix 66, and portion 29 of second coiled lead 28 is shaped to define a second helix 68. In other words, portions 29 and 36 comprise longitudinal elements shaped to define respective helices that are not covered by non-helical sheaths. In such applications, portion 29 of the second lead is aligned with respect to portion 36 of the first lead by laterally squeezing together the portion of the second lead with the portion of the first lead, such that the helical turns of the second lead are interdigitated with the helical turns of the first lead, and central longitudinal axis 31 of the second lead passes through portion 36. (Hence, a pacing signal passing through one of the leads induces a synchronization signal in the other one of the leads, as described hereinabove.) In some applications, as shown in FIG. 7, portion 36 is disposed proximally to the first IPG, and portion 29 is disposed proximally to the second IPG. In other applications, at least one of portions 29 and 36 is disposed distally to the IPG to which it is connected.

To facilitate the lateral squeezing-together of the two portions of the respective leads, the pitch P0 of the first helix is typically (but not necessarily) generally equal to the pitch P1 of the second helix, when no longitudinal force is applied to the first helix and no longitudinal force is applied to the second helix. Furthermore, the space S0 between consecutive turns of the first helix is typically between 0.5 and 1.5 times a diameter D0 of the longitudinal element of the second lead, when no longitudinal force is applied to the first helix. This ratio facilitates the squeezing-together of the two helices, and/or helps the two helices remain squeezed together by allowing for sufficient frictional force between the interdigitated turns of the helices. Further facilitating the squeezing-together, as rioted above, is the lack of non-helical sheaths surrounding the respective helices.

In some applications, as shown in FIG. 8, the portion of the second lead is laterally squeezed together with the portion of the first lead by passing a hollow structure 70 over the portion of the second lead and the portion of the first lead. In some applications, to facilitate communication between the two leads, ferrite core 72 is inserted into the common lumen of portions 29 and 36, following the squeezing together of the two portions. The insertion of ferrite core 72 may also help keep the squeezed-together portions from coming apart, i.e., it may help maintain the interdigitation of the helical turns of the second lead with the helical turns of the first lead. Alternatively or additionally, a locking mechanism 73 that maintains the interdigitation of the helical turns of the second lead with the helical turns of the first lead may be activated. For example, a clasp may be placed over the squeezed-together portions, and/or a locking mechanism that is integrated with one or both of the leads may be automatically activated by the squeezing-together of the two portions. In some applications, the locking mechanism permanently locks the two portions together, i.e., the locking mechanism cannot be deactivated without breaking the locking mechanism. Alternatively or additionally, a sheath 71 (which may be identical to hollow structure 70) may be placed over the portion of the second lead and the portion of the first lead, thus maintaining the interdigitation of the helical turns of the second lead with the helical turns of the first lead.

Figure 9A:
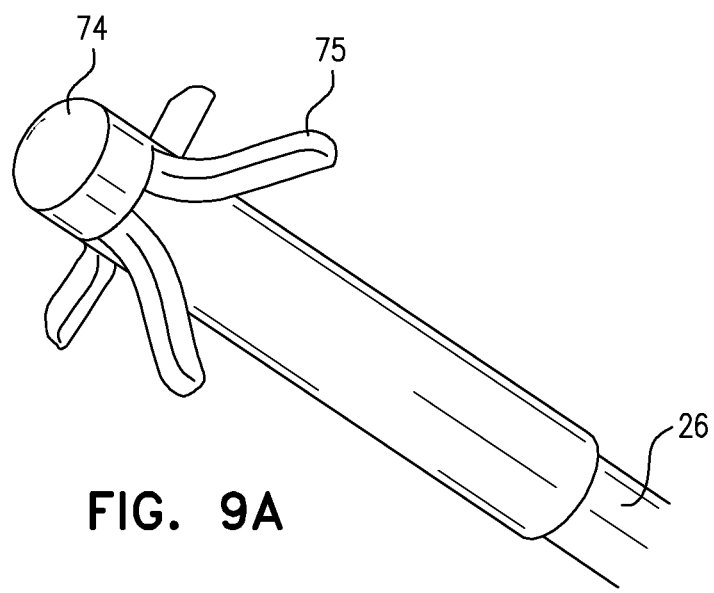
FIGS. 9A-B are schematic illustrations of respective distal ends of leads, in accordance with some applications of the present invention.
Figure 9B:
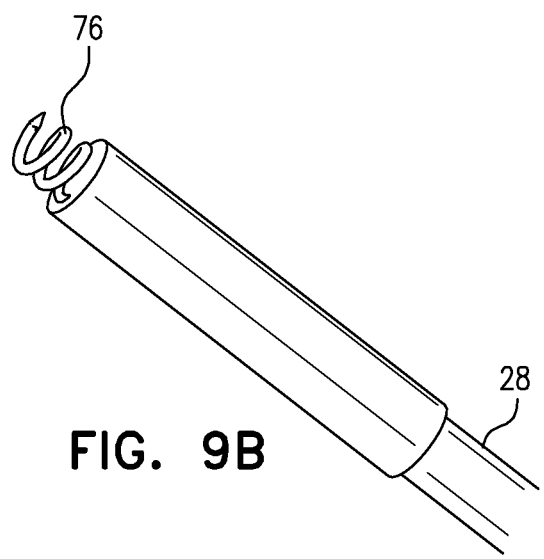

Reference is now made to FIGS. 9A-B, which are schematic illustrations of respective distal ends of leads 26 and 28, in accordance with some applications of the present invention. Typically, a tined anchor 74, comprising tines 75, is used to anchor the distal end of one of the leads in the right atrium, while a screw anchor 76 is used to anchor the distal end of the other one of the leads in the right ventricle. Typically, the first lead is implanted in the right atrium using the tined anchor, while the second lead is implanted in the right ventricle using the screw anchor. Using the screw anchor for implantation of the second lead, rather than for the first lead, is generally preferred for applications in which the second lead is passed through the larger-diameter coiled portion of the first lead, since the tined anchor may not pass through the larger-diameter coiled portion.

It is noted that the scope of the present invention includes interchanging the implantation locations (i.e., implanting the first lead in the right ventricle, and the second lead in the right atrium), implanting both of the leads in the same chamber of the heart, and/or implanting one or both of the leads on the left side of the heart. Furthermore, the scope of the present invention includes interchanging the types of anchors used at each implantation location, or using different types of anchors not explicitly described herein.

Figure 10:
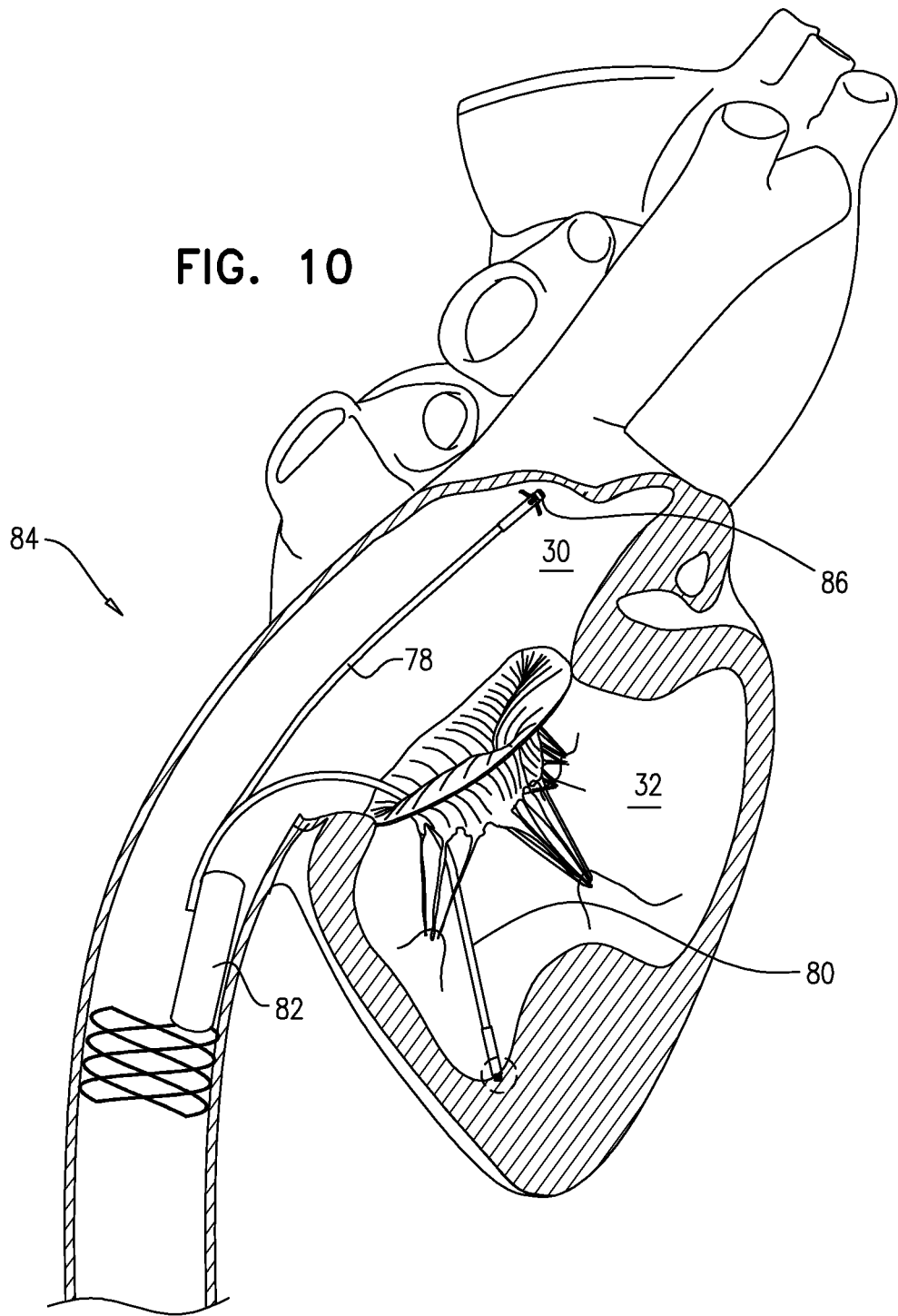
FIGS. 10-11 are schematic illustrations of apparatus for pacing a heart of a subject, in accordance with some applications of the present invention.

Reference is now made to FIG. 10, which is a schematic illustration of apparatus 84 for pacing a heart of a subject, in accordance with some applications of the present invention. Apparatus 84 comprises an IPG 82 connected to a first lead 78 and a second lead 80. IPG 82 is implanted in the superior or inferior vena cava of the subject, typically near the sinoatrial node 86. The first lead is implanted at the sinoatrial node 86, while the second lead is implanted in the right ventricle. (While FIG. 10 shows a tined anchor at the distal end of first lead 78, it is noted that other types of anchors may also be used to anchor first lead 78 at sinoatrial node 86.)

As noted above in the Summary, when using a single IPG with multiple standard leads, it is typically difficult to choose an implantation location for the IPG, and/or lead lengths, such that each of the leads can reach its designated pacing site without leaving too much slack. Some applications of the present invention address this problem, by providing a first lead 78 that is relatively springy. The implantation location of the IPG may be "matched" to the length of the second lead, and, as long as the IPG is close enough to sinoatrial node 86, the first lead will spring into place, without leaving too much slack. ("Matching" the implantation location of the IPG to the length of the second lead means that the IPG is implanted at a location that is (i) close enough to the implantation location of the second lead to allow the second lead to reach the implantation location of the second lead, yet (ii) far enough from the implantation location of the second lead to allow the second lead to be relatively taut.)

Figure 11:
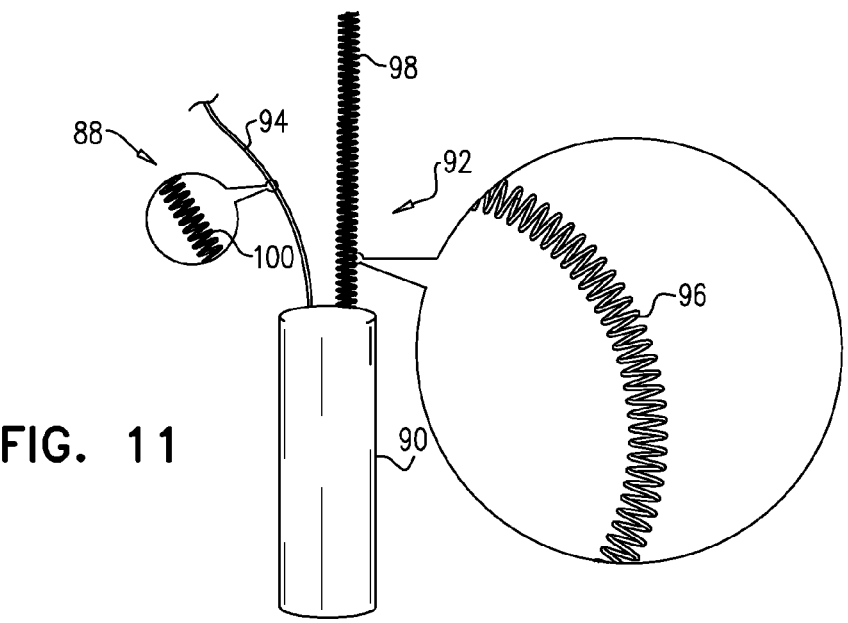

Reference is now made to FIG. 11, which is a schematic illustration of apparatus 88 for pacing a heart of a subject, in accordance with some applications of the present invention. Apparatus 88 comprises an IPG 90, a first lead 92 connected to IPG 90, and a second lead 94 connected to IPG 90. First lead 92 comprises a longitudinal, element coiled to define a first helix 96, first helix 96 being coiled to define a second helix 98. (The significance of the structure of first lead 92 is described immediately hereinbelow, with reference to FIG. 12.) Typically, second lead 94 also comprises a longitudinal element coiled to define a "first" helix 100, but helix 100 is not coiled to define a second helix. (In other words, second lead 94 is typically structurally similar to the coiled leads described hereinabove, with reference to previous figures.) Typically, a screw anchor 76 (FIG. 9B) is disposed at the distal end of the first lead, and/or a tined anchor 74 (FIG. 9A) is disposed at the distal end of the second lead. The first lead is typically implanted in the right ventricle (e.g., by turning the screw anchor into the tissue of the right ventricle), while the second lead is typically implanted in the right atrium (e.g., by implanting the tined anchor).

Figure 12:
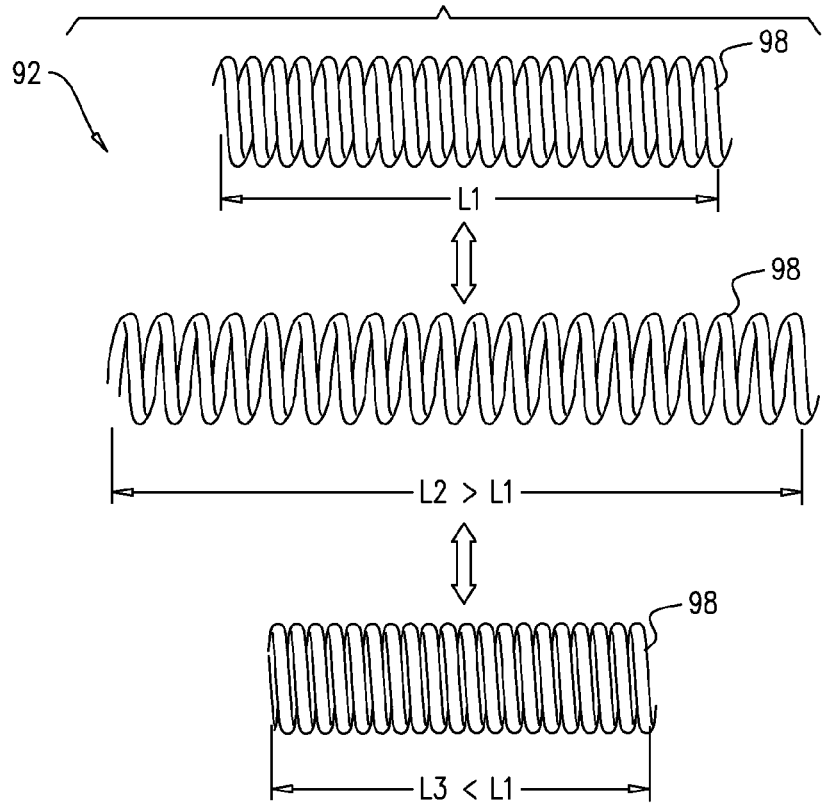
FIG. 12 is a schematic illustration of a lead, in accordance with some applications of the present invention.

Reference is now made to FIG. 12, which is a schematic illustration of first lead 92, in accordance with some applications of the present invention. First lead 92 has a "resting" length L1 when no stretching or compressive forces are applied to the first lead (top). By stretching second helix 98, the length of the first lead may be increased to L2, which is greater than length L1 (middle). Conversely, by compressing second helix 98, the length of the first lead may be decreased to L3, which is less than resting length L1 (bottom). Hence, the length of the first lead is adjustable. As noted above in the Summary, when using a single implantable pulse generator (IPG) with multiple standard leads, it is typically difficult to choose an implantation location for the IPG, and/or lead lengths, such that each of the leads can reach its designated pacing site without leaving too much slack. The adjustable length of the first lead addresses this difficulty, as it removes, to a certain extent, the need to "match" the implantation location of the IPG to the length of the first lead. In other words, the implantation location of the IPG may be matched to the length of the second lead, and the length of the first lead will change (i.e., increase or decrease) accordingly.

Typically, the length of first helix 96 does not substantially change, even when the first lead is stretched or compressed. In other words, the adjustability of the length of the first lead is generally due only to the adjustability of the length of second helix 98.

Figure 13A:
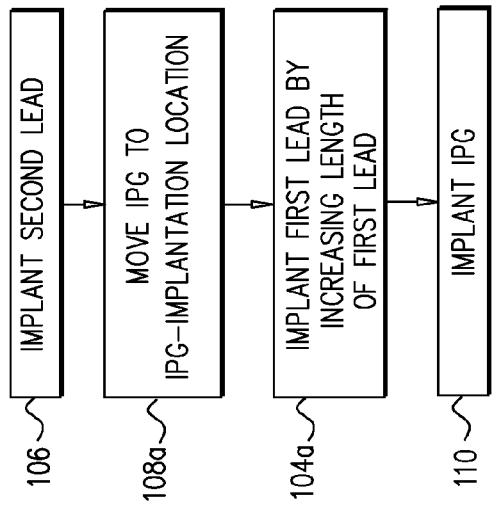
FIGS. 13A-C show respective flow charts for various implantation procedures, in accordance with some applications of the present invention.
Figure 13B:
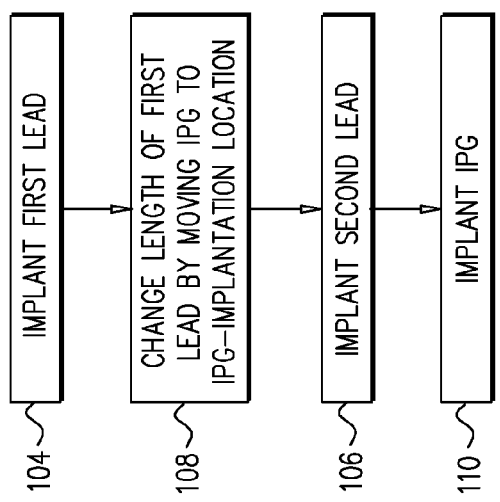

Reference is now made to FIGS. 13A-B, which show respective flow charts for various implantation procedures, in accordance with some applications of the present invention. In some applications, the length of the first lead is changed by moving the IPG to the IPG-implantation location. That is, after implanting the first lead at a first-lead-implantation step 104, the IPG is moved to the IPG-implantation location at an IPG-moving step 108, thus stretching or compressing the first lead. In such applications, the second lead may be implanted before or after the moving of the IPG to the IPG-implantation location. FIG. 13A shows a second-lead-implantation step 106 performed before IPG-moving step 108, while FIG. 13B shows second-lead-implantation step 106 performed after IPG-moving step 108. The IPG is typically implanted only after the implantation of both of the leads, i.e., an IPG-implantation step 110 is performed only at the end of the implantation procedure.

If the distance between the IPG-implantation location and the implantation location of the first lead is greater than L1 (FIG. 12), the first lead will be stretched as the IPG is moved to the I?G-implantation location. Conversely, if the distance between the IPG-implantation location and the implantation location of the first lead is less than L1, the first lead will be compressed as the IPG is moved to the IPG-implantation location.

Figure 13C:
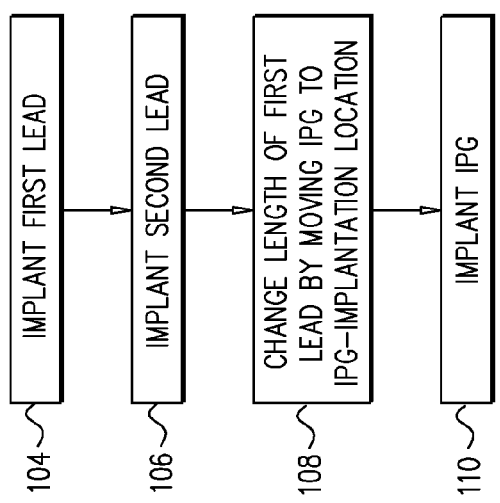
Figure 14:
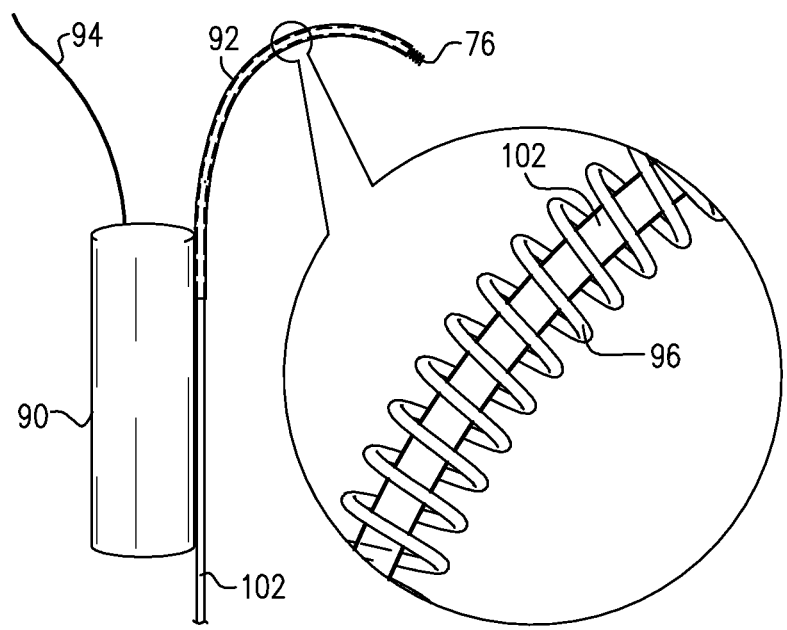
FIG. 14 is a schematic illustration showing the implantation of a lead, in accordance with some applications of the present invention.

Reference is now made to FIG. 13C, which shows a flow chart for an implantation procedure, in accordance with some applications of the present invention. Reference is additionally made to FIG. 14, which is a schematic illustration showing the implantation of first lead 92, in accordance with some applications of the present invention.

In some applications, the first lead is implanted by increasing the length of the first lead, i.e., increasing the length of the second helix. For example, a stylet 102 may be inserted into the lumen of first helix 96, and stylet 102 may be used to push the distal end of the first lead to the implantation location of the first lead. As the stylet pushes the distal end of the first lead, the length of the second helix is increased. (In some applications, the pushing with the stylet causes the second helix to become substantially straightened, as shown in FIG. 14, such that first lead 92 resembles second lead 94.) Typically, the stylet is removed from the lumen of the first helix after implanting the first lead and before implanting the second lead.

In some applications, the first lead is implanted, by being stretched, following the moving of the IPG to the IPG-implantation location. This scenario is depicted in the flow chart of FIG. 13C, which shows a first-lead-implantation step 104a occurring after an IPG-moving step 108a. In other applications, following the implantation of the first lead by being stretched, the IPG is moved to the IPG-implantation location, thus further increasing, or alternatively, decreasing, the length of the first lead, as described hereinabove. (As noted above, the second lead may be implanted before or after the moving of the IPG to the IPG-implantation location.) These scenarios may be depicted in slight modifications (not shown) of FIGS. 13A and 13B, respectively, in which first-lead-implantation step 104a (which includes stretching of the first lead) takes the place of first-lead-implantation step 104 (which does not include stretching of the first lead).

In some applications, stylet 102 is used to turn screw anchor 76 disposed at the distal end of the first lead. For example, after using the stylet to push the distal end of the first lead to the implantation location of the first lead, as described hereinabove, the stylet may be used to turn the screw anchor. Alternatively or additionally, the screw anchor may be turned by rotating the IPG, the first lead, and the second lead around the central longitudinal axis of the first lead.

Figure 15:
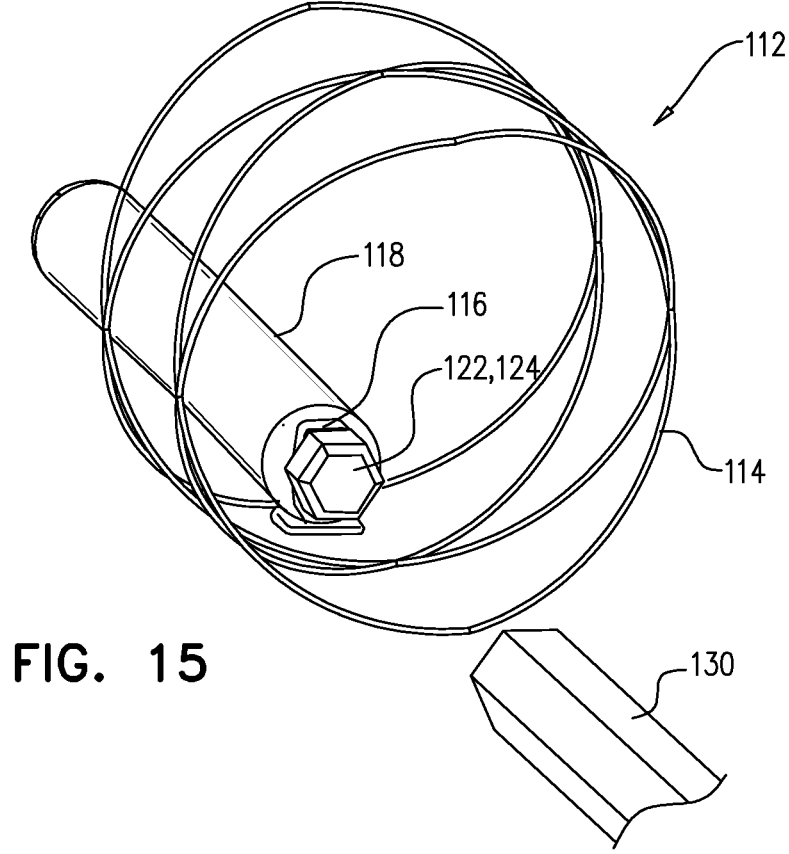
FIG. 15 is a schematic illustration of apparatus for implantation in a blood vessel of a subject, in accordance with some applications of the present invention.
Figure 16:
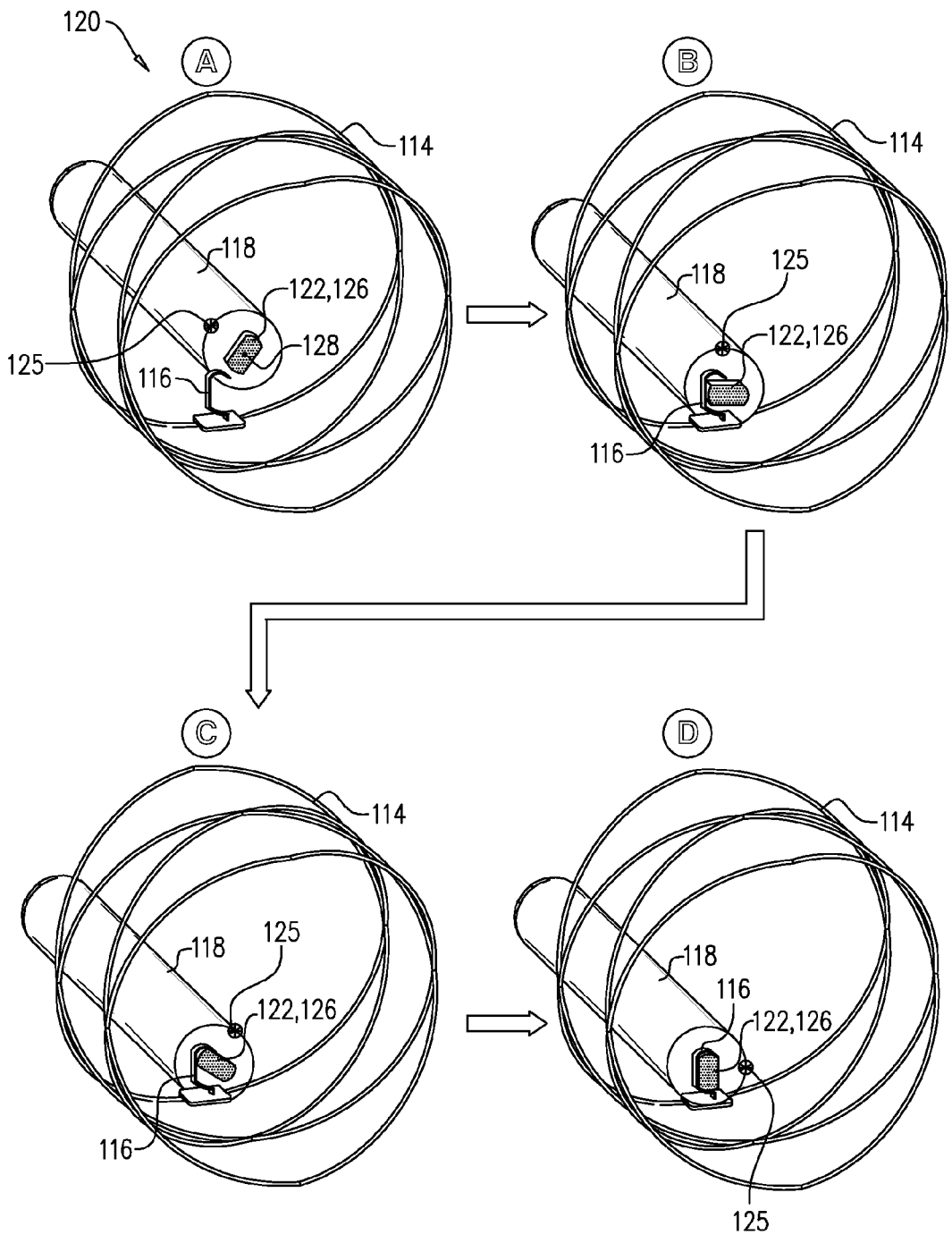
FIG. 16 shows a method for coupling an IPG to a stent, in accordance with some applications of the present invention.

Reference is now made to FIG. 15, which is a schematic illustration of apparatus 112 for implantation in a blood vessel of a subject, in accordance with some applications of the present invention. Apparatus 112 comprises an intravascular stent 114 shaped to define a socket 116, and an IPG 118. Reference is also made to FIG. 16, which shows a method for coupling IPG 118 to stent 114, in accordance with some applications of the present invention. As shown in FIGS. 15-16, IPG 118 is shaped to define a bolt 122 that is shaped to be secured by socket 116. (The long cylindrical body shown in FIGS. 15-16 is the main portion of the IPG; bolt 122 is shown protruding from the front-facing end of the cylindrical body.) Typically, bolt 122 comprises a bolt body 126 shaped to be received by the socket, and a bolt cap 124 shaped to inhibit release of the bolt from the socket. Bolt cap 124 is typically not removable from the bolt; for ease of illustration, however, FIG. 16 shows the bolt without the bolt cap.

In method 120, IPG 118 is coupled to the stent, by securing the bolt in the socket. In some applications, the bolt is secured in the socket by inserting the bolt into the socket from a direction that is substantially perpendicular to a central longitudinal axis 128 of the bolt. In the context of the claims and description of the present application, the central longitudinal axis of the bolt is the central axis passing through the bolt and running through the IPG, or alongside the main axis of the IPG. Thus, step A in FIG. 16 shows central longitudinal axis 128 running into the page, and FIG. 16 shows the bolt inserted into the socket from the sideways direction, which is substantially perpendicular to central longitudinal axis 128.

Alternatively or additionally, the bolt is inserted into the socket by rotating the IPG around central longitudinal axis 128. This is depicted in FIG. 16, in which each of steps A-D shows a different stage of the rotation. (To help show the rotation of the IPG, a hypothetical mark 125 is marked on the circumference of the IPG in each of steps A-D.)

In general, IPG 118 may be uncoupled from stent 114 by reversing the steps performed in method 120. For example, to uncouple the IPG from the stent, the IPG may be rotated around central longitudinal axis 128, in the opposite direction from which it was rotated during the coupling of the IPG to the stent. (FIG. 16 depicts a clockwise rotation for coupling, and a counterclockwise rotation for uncoupling.) Similarly, to remove the bolt from the socket, the bolt may be moved in a direction that is substantially perpendicular to central longitudinal axis 128, and is opposite the direction in which it was moved during the coupling of the IPG to the stent.

An advantage of apparatus 112 is that the IPG may be removed from the body of the subject without removing the stent. (Implanted stents are typically difficult to remove from blood vessels, due to growth of tissue around the stent.) For example, if IPG 118 has an internal battery that is running low, the IPG may be removed from the subject, in order to replace the battery. Subsequently to replacing the battery, the IPG may be recoupled to the stent, by securing the bolt in the socket. Alternatively, the first IPG may be permanently removed from the subject, and a second IPG may be coupled to the stent by securing a bolt of the second IPG in the socket.

Typically, following the coupling of the IPG to the stent, the IPG is implanted in a blood vessel of a subject, by expanding the stent. In some applications, however, the IPG is coupled to the stent while the stent is implanted in a blood vessel of the subject. For example, as described immediately above, following the replacement of the IPG battery, the IPG may be recoupled to the stent while the stent is already implanted in the blood vessel.

In some applications, to uncouple the IPG from the stent, a tool 130 is inserted into the blood vessel, and using the tool, the bolt is removed from the socket. In some applications, as shown in FIG. 15, bolt cap 124 facilitates the uncoupling of the IPG from the stent (and/or the coupling of the IPG to the stent), by providing a grip for tool 130.

In general, apparatus 112 may be used, and method 120 may be practiced, in combination with any of the applications described hereinabove. For example, IPG 118 may be used for first IPG 22 and/or second IPG 24 of FIG. 1, stent 114 being used for stent 50.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for pacing a heart of a subject, the apparatus comprising a kit comprising:
   (a) a first implantable pulse generator (IPG); and
   (b) a first coiled lead connected to the first IPG, the first coiled lead comprising:
      a smaller-diameter coiled portion, a lumen of which having a first coillumen-diameter; and
      a larger-diameter coiled portion electrically in series with the smaller-diameter coiled portion, a lumen of the larger-diameter coiled portion having a second coil-lumen-diameter that is larger than the first coil-lumen-diameter,
      a perpendicular distance from a central longitudinal axis of the smaller-diameter coiled portion to the lumen of the larger-diameter coiled portion being greater than an outer radius of the smaller-diameter coiled portion, when the central longitudinal axis of the smaller-diameter coiled portion is parallel to a central longitudinal axis of the larger-diameter coiled portion;
   (c) a second IPG, which is not electrically or mechanically coupled to the first IPG when contained inside the kit; and
   (d) a second coiled lead connected to the second IPG, an outer diameter of the second coiled lead being less than the diameter of the lumen of the larger-diameter coiled portion of the first coiled lead,
   wherein when a portion of the second coiled lead is aligned with respect to the larger-diameter coiled portion of the first coiled lead such that a central longitudinal axis of the portion of the second coiled lead passes longitudinally through the larger-diameter coiled portion of the first coiled lead:
      one of the first and the second IPGs is configured to generate a first pacing signal, which passes through its coiled lead and induces a synchronizing signal in the other coiled lead, and
      the other one of the first and the second IPGs is configured to receive the synchronizing signal, and generate a second pacing signal in response to the synchronizing signal.

2. The apparatus according to claim 1, wherein a perpendicular distance between:
   (a) a central longitudinal axis of the first IPG and
   (b) the central longitudinal axis of the smaller-diameter coiled portion is greater than a perpendicular distance between:
   (a) the central longitudinal axis of the first IPG and
   (b) the central longitudinal axis of the larger-diameter coiled portion,
   when the central longitudinal axis of the first IPG is parallel to (i) the central longitudinal axis of the larger-diameter coiled portion, and (ii) the central longitudinal axis of the smaller-diameter coiled portion.

3. The apparatus according to claim 1, wherein a perpendicular distance between:
   (a) a central longitudinal axis of the first IPG and
   (b) the central longitudinal axis of the larger-diameter coiled portion is greater than a perpendicular distance between:
   (a) the central longitudinal axis of the first IPG and
   (b) the central longitudinal axis of the smaller-diameter coiled portion,
   when the central longitudinal axis of the first IPG is parallel to (i) the central longitudinal axis of the larger-diameter coiled portion, and (ii) the central longitudinal axis of the smaller-diameter coiled portion.

4. The apparatus according to claim 1, wherein
   (i) a central longitudinal axis of the first IPG,
   (ii) the central longitudinal axis of the smaller-diameter coiled portion, and
   (iii) the central longitudinal axis of the larger-diameter coiled portion are not all coplanar with each other.

5. The apparatus according to claim 1, wherein a perpendicular distance from a central longitudinal axis of the first IPG to the lumen of the larger-diameter coiled portion is greater than an outer radius of the first IPG, when the first coiled lead is straight.

6. The apparatus according to claim 1, wherein a perpendicular distance from a central longitudinal axis of the first IPG to the lumen of the smaller-diameter coiled portion is greater than an outer radius of the first IPG, when the central longitudinal axis of the first IPG is parallel to the central longitudinal axis of the smaller-diameter coiled portion.

7. The apparatus according to claim 1, wherein the first IPG is shaped to define a channel, a proximal portion of the smaller-diameter coiled portion being disposed within the channel.

8. The apparatus according to claim 1, wherein the smaller-diameter coiled portion is disposed longitudinally between the first IPG and the larger-diameter coiled portion.

9. The apparatus according to claim 8,
wherein the smaller-diameter coiled portion is a first smaller-diameter coiled portion,
wherein the first coiled lead further comprises a second smaller-diameter coiled portion electrically in series with the larger-diameter coiled portion, a lumen of the second smaller-diameter coiled portion having a diameter that is less than the diameter of the lumen of the larger-diameter coiled portion,
wherein the larger-diameter coiled portion is disposed between the first smaller-diameter coiled portion and the second smaller-diameter coiled portion, and
wherein a perpendicular distance from a central longitudinal axis of the second smaller-diameter coiled portion to the lumen of the larger-diameter coiled portion is greater than an outer radius of the second smaller-diameter coiled portion, when the central longitudinal axis of the second smaller-diameter coiled portion is parallel to the central longitudinal axis of the larger-diameter coiled portion.

10. The apparatus according to claim 1, wherein the larger-diameter coiled portion is disposed longitudinally between the first IPG and the smaller-diameter coiled portion.

11. The apparatus according to claim 1, further comprising an intravascular stent, the first IPG being coupled to the stent.

12. The apparatus according to claim 1, wherein an outer diameter of the second coiled lead is constant over at least 95% of a length of the second coiled lead.

13. The apparatus according to claim 1, wherein a length of the larger-diameter coiled portion of the first coiled lead is 0.5-5 cm.

14. The apparatus according to claim 13, wherein the length of the larger-diameter coiled portion of the first coiled lead is 1-3 cm.

15. The apparatus according to claim 1, wherein a proximal end of the larger-diameter coiled portion has a funnel-shaped configuration.

16. The apparatus according to claim 15, wherein the proximal end of the larger-diameter coiled portion is configured to have (i) a collapsed configuration when disposed inside of an enclosing lumen, and (ii) the funnel-shaped configuration when not disposed inside of the enclosing lumen.

17. The apparatus according to claim 1, further comprising a flexible longitudinal element passing through the larger-diameter coiled portion.

18. The apparatus according to claim 17, wherein the flexible longitudinal element is shaped as a loop.

19. The apparatus according to claim 1, wherein the first and the second coiled leads are covered by respective non-helical casings.

20. Apparatus for pacing a heart of a subject, the apparatus comprising:
an implantable pulse generator (IPG), configured to generate a pacing signal;
a coiled lead connected to the IPG, the coiled lead comprising:
a smaller-diameter coiled portion, a lumen of which having a first coil-lumen-diameter; and
a larger-diameter coiled portion electrically in series with the smaller-diameter coiled portion, a lumen of the larger-diameter coiled portion having a second coil-lumen-diameter that is larger than the first coil-lumen-diameter,
a perpendicular distance from a central longitudinal axis of the smaller-diameter coiled portion to the lumen of the larger-diameter coiled portion being greater than an outer radius of the smaller-diameter coiled portion, when the central longitudinal axis of the smaller-diameter coiled portion is parallel to a central longitudinal axis of the larger-diameter coiled portion;
a flexible longitudinal element passing through the larger-diameter coiled portion,
wherein the flexible longitudinal element is shaped as a loop, and
wherein the flexible longitudinal element loops around the smaller-diameter coiled portion.

21. A method for pacing a heart of a subject, the method comprising:
providing a kit comprising:
(a) a first implantable pulse generator (IPG); and
(b) a first coiled lead connected to the first IPG, the first coiled lead comprising:
a smaller-diameter coiled portion, a lumen of which having a first coil-lumen-diameter; and
a larger-diameter coiled portion electrically in series with the smaller-diameter coiled portion, a lumen of the larger-diameter coiled portion having a second coil-lumen-diameter that is larger than the first coil-lumen-diameter, a perpendicular distance from a central longitudinal axis of the smaller-diameter coiled portion to the lumen of the larger-diameter coiled portion being greater than an outer radius of the smaller-diameter coiled portion, when the central longitudinal axis of the smaller-diameter coiled portion is parallel to a central longitudinal axis of the larger-diameter coiled portion;
(c) a second IPG, which is not electrically or mechanically coupled to the first IPG when contained inside the kit; and
(d) a second coiled lead connected to the second IPG, an outer diameter of the second coiled lead being less than the diameter of the lumen of the larger-diameter coiled portion of the first coiled lead;
implanting a distal end of the first coiled lead at a first location in a heart of the subject;
implanting the first IPG in a blood vessel of the subject;
implanting a distal end of the second coiled lead at a second location in the heart of the subject;
implanting the second IPG in the blood vessel of the subject; and
aligning a portion of the second coiled lead with respect to the larger-diameter coiled portion of the first coiled lead such that a central longitudinal axis of the portion of the second coiled lead passes longitudinally through the larger-diameter coiled portion of the first coiled lead, wherein when the portion of the second coiled lead is aligned with respect to the larger-diameter coiled portion of the first coiled lead such that the central longitudinal axis of the portion of the second coiled lead passes longitudinally through the larger-diameter coiled portion of the first coiled lead:

one of the first and the second IPGs is configured to generate a first pacing signal, which passes through its coiled lead and induces a synchronizing signal in the other coiled lead, and the other one of the first and the second IPGs is configured to receive the synchronizing signal, and generate a second pacing signal in response to the synchronizing signal.

\* \* \* \* \*